United States Patent
Rockrohr et al.

(10) Patent No.: US 10,682,146 B2
(45) Date of Patent: Jun. 16, 2020

(54) SURGICAL CLIP APPLIER

(71) Applicant: Covidien LP, Mansfield, MA (US)

(72) Inventors: Brian Rockrohr, Guilford, CT (US); Jaroslaw T. Malkowski, Trumbull, CT (US)

(73) Assignee: COVIDIEN LP, Mansfield, MA (US)

( * ) Notice: Subject to any disclaimer, the term of this patent is extended or adjusted under 35 U.S.C. 154(b) by 337 days.

(21) Appl. No.: 15/692,602

(22) Filed: Aug. 31, 2017

(65) Prior Publication Data

US 2017/0360449 A1 Dec. 21, 2017

Related U.S. Application Data

(62) Division of application No. 14/315,508, filed on Jun. 26, 2014, now Pat. No. 9,775,624.

(60) Provisional application No. 61/870,404, filed on Aug. 27, 2013.

(51) Int. Cl.
 *A61B 17/128* (2006.01)
(52) U.S. Cl.
 CPC ........ *A61B 17/1285* (2013.01); *A61B 17/128* (2013.01)
(58) Field of Classification Search
 CPC .......................... A61B 17/1285; A61B 17/128
 See application file for complete search history.

(56) References Cited

U.S. PATENT DOCUMENTS

| | | | |
|---|---|---|---|
| 3,120,230 A | 2/1964 | Skold | |
| 3,363,628 A | 1/1968 | Wood | |
| 3,638,847 A | 2/1972 | Noiles et al. | |
| 3,867,944 A | 2/1975 | Samuels | |
| 4,226,242 A | 10/1980 | Jarvik | |
| 4,242,902 A | 1/1981 | Green | |
| 4,296,751 A | 10/1981 | Blake, III et al. | |
| 4,372,316 A | 2/1983 | Blake, III et al. | |
| 4,408,603 A | 10/1983 | Blake, III et al. | |
| 4,412,539 A | 11/1983 | Jarvik | |
| 4,418,694 A | 12/1983 | Beroff et al. | |
| 4,425,915 A | 1/1984 | Ivanov | |

(Continued)

FOREIGN PATENT DOCUMENTS

| AU | 2010200641 A1 | 10/2010 |
|---|---|---|
| AU | 2013254887 A1 | 11/2013 |

(Continued)

OTHER PUBLICATIONS

The Extended European Search Report corresponding to EP 13 16 6382.5, completed Nov. 19, 2013 and dated Nov. 28, 2013; (8 Pages).

(Continued)

*Primary Examiner* — Jing Rui Ou

(57) ABSTRACT

A surgical clip applier is provided including a clip pusher bar having a flexible tab and a camming plate configured to effectuate closure of the pair of jaws. The camming plate includes a lost motion portion and the flexible tab is configured to engage the lost motion portion during an initial movement of the clip pusher bar to cause the camming plate to move with the clip pusher bar. The flexible tab is configured to disengage from the lost motion portion during a subsequent movement of the clip pusher bar to allow the clip pusher bar to move relative to the camming plate.

10 Claims, 8 Drawing Sheets

(56) References Cited

U.S. PATENT DOCUMENTS

| | | |
|---|---|---|
| 4,427,008 A | 1/1984 | Transue |
| 4,449,531 A | 5/1984 | Cerwin et al. |
| 4,471,780 A | 9/1984 | Menges et al. |
| 4,478,220 A | 10/1984 | Di Giovanni et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,592,498 A | 6/1986 | Braun et al. |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,726,372 A | 2/1988 | Perlin |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,951,860 A | 8/1990 | Peters et al. |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,359,993 A | 11/1994 | Slater et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |

(56) References Cited

U.S. PATENT DOCUMENTS

| | | |
|---|---|---|
| 5,448,042 A | 9/1995 | Robinson et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,562,655 A | 10/1996 | Mittelstadt et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,743,310 A | 4/1998 | Moran |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,991 A | 7/1999 | Whitehead et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,044,971 A | 4/2000 | Esposito et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |

(56) References Cited

U.S. PATENT DOCUMENTS

| | | | |
|---|---|---|---|
| 6,607,540 | B1 | 8/2003 | Shipp |
| 6,613,060 | B2 | 9/2003 | Adams et al. |
| 6,626,916 | B1 | 9/2003 | Yeung et al. |
| 6,626,922 | B1 | 9/2003 | Hart et al. |
| 6,648,898 | B1 | 11/2003 | Baxter |
| 6,652,538 | B2 | 11/2003 | Kayan et al. |
| 6,652,539 | B2 | 11/2003 | Shipp et al. |
| 6,656,193 | B2 | 12/2003 | Grant et al. |
| 6,673,083 | B1 | 1/2004 | Kayan et al. |
| 6,676,659 | B2 | 1/2004 | Hutchins et al. |
| 6,679,894 | B2 | 1/2004 | Damarati |
| RE38,445 | E | 2/2004 | Pistl et al. |
| 6,695,854 | B1 | 2/2004 | Kayan et al. |
| 6,706,057 | B1 | 3/2004 | Bidoia et al. |
| 6,716,226 | B2 | 4/2004 | Sixto, Jr. et al. |
| 6,723,109 | B2 | 4/2004 | Solingen |
| 6,743,240 | B2 | 6/2004 | Smith et al. |
| 6,773,438 | B1 | 8/2004 | Knodel et al. |
| 6,773,440 | B2 | 8/2004 | Gannoe et al. |
| 6,776,783 | B1 | 8/2004 | Frantzen et al. |
| 6,776,784 | B2 | 8/2004 | Ginn |
| 6,780,195 | B2 | 8/2004 | Porat |
| 6,793,663 | B2 | 9/2004 | Kneifel et al. |
| 6,793,664 | B2 | 9/2004 | Mazzocchi et al. |
| 6,802,848 | B2 | 10/2004 | Anderson et al. |
| 6,814,742 | B2 | 11/2004 | Kimura et al. |
| 6,818,009 | B2 | 11/2004 | Hart et al. |
| 6,821,273 | B2 | 11/2004 | Mollenauer |
| 6,821,284 | B2 | 11/2004 | Sturtz et al. |
| 6,824,547 | B2 | 11/2004 | Wilson, Jr. et al. |
| 6,824,548 | B2 | 11/2004 | Smith et al. |
| 6,835,199 | B2 | 12/2004 | McGuckin, Jr. et al. |
| 6,835,200 | B2 | 12/2004 | Laufer et al. |
| 6,837,893 | B2 | 1/2005 | Miller |
| 6,837,894 | B2 | 1/2005 | Pugsley, Jr. et al. |
| 6,837,895 | B2 | 1/2005 | Mayenberger |
| 6,840,945 | B2 | 1/2005 | Manetakis et al. |
| 6,843,794 | B2 | 1/2005 | Sixto, Jr. et al. |
| 6,849,078 | B2 | 2/2005 | Durgin et al. |
| 6,849,079 | B1 | 2/2005 | Blake, III et al. |
| 6,853,879 | B2 | 2/2005 | Sunaoshi |
| 6,869,435 | B2 | 3/2005 | Blake, III |
| 6,869,436 | B2 | 3/2005 | Wendlandt |
| 6,889,116 | B2 | 5/2005 | Jinno |
| 6,896,682 | B1 | 5/2005 | McClellan et al. |
| 6,905,503 | B2 | 6/2005 | Gifford, III et al. |
| 6,911,032 | B2 | 6/2005 | Jugenheimer et al. |
| 6,911,033 | B2 | 6/2005 | de Guillebon et al. |
| 6,913,607 | B2 | 7/2005 | Ainsworth et al. |
| 6,916,327 | B2 | 7/2005 | Northrup, III et al. |
| 6,923,818 | B2 | 8/2005 | Muramatsu et al. |
| 6,939,356 | B2 | 9/2005 | Debbas |
| 6,942,674 | B2 | 9/2005 | Belef et al. |
| 6,942,676 | B2 | 9/2005 | Buelna |
| 6,945,978 | B1 | 9/2005 | Hyde |
| 6,945,979 | B2 | 9/2005 | Kortenbach et al. |
| 6,949,107 | B2 | 9/2005 | McGuckin, Jr. et al. |
| 6,953,465 | B2 | 10/2005 | Dieck et al. |
| 6,955,643 | B2 | 10/2005 | Gellman et al. |
| 6,959,852 | B2 | 11/2005 | Shelton, IV et al. |
| 6,960,218 | B2 | 11/2005 | Rennich |
| 6,960,221 | B2 | 11/2005 | Ho et al. |
| 6,962,594 | B1 | 11/2005 | Thevenet |
| 6,963,792 | B1 | 11/2005 | Green |
| 6,964,363 | B2 | 11/2005 | Wales et al. |
| 6,964,668 | B2 | 11/2005 | Modesitt et al. |
| 6,966,875 | B1 | 11/2005 | Longobardi |
| 6,966,917 | B1 | 11/2005 | Suyker et al. |
| 6,966,919 | B2 | 11/2005 | Sixto, Jr. et al. |
| 6,969,391 | B1 | 11/2005 | Gazzani |
| 6,972,023 | B2 | 12/2005 | Whayne et al. |
| 6,972,027 | B2 | 12/2005 | Fallin et al. |
| 6,973,770 | B2 | 12/2005 | Schnipke et al. |
| 6,974,462 | B2 | 12/2005 | Sater |
| 6,974,466 | B2 | 12/2005 | Ahmed et al. |
| 6,974,475 | B1 | 12/2005 | Wall |
| 6,981,505 | B2 | 1/2006 | Krause et al. |
| 6,981,628 | B2 | 1/2006 | Wales |
| 6,991,635 | B2 | 1/2006 | Takamoto et al. |
| 7,052,504 | B2 | 5/2006 | Hughett |
| 7,056,330 | B2 | 6/2006 | Gayton |
| 7,108,703 | B2 | 9/2006 | Danitz et al. |
| 7,144,402 | B2 | 12/2006 | Kuester, III |
| 7,175,648 | B2 | 2/2007 | Nakao |
| 7,179,265 | B2 | 2/2007 | Manetakis et al. |
| 7,207,997 | B2 | 4/2007 | Shipp et al. |
| 7,211,091 | B2 | 5/2007 | Fowler et al. |
| 7,211,092 | B2 | 5/2007 | Hughett |
| 7,214,230 | B2 | 5/2007 | Brock et al. |
| 7,214,232 | B2 | 5/2007 | Bowman et al. |
| 7,223,271 | B2 | 5/2007 | Muramatsu et al. |
| 7,232,445 | B2 | 6/2007 | Kortenbach et al. |
| 7,261,724 | B2 | 8/2007 | Molitor et al. |
| 7,261,725 | B2 | 8/2007 | Binmoeller |
| 7,264,625 | B1 | 9/2007 | Buncke |
| 7,288,098 | B2 | 10/2007 | Huitema et al. |
| 7,297,149 | B2 | 11/2007 | Vitali et al. |
| 7,316,693 | B2 | 1/2008 | Viola |
| 7,316,696 | B2 | 1/2008 | Wilson, Jr. et al. |
| 7,326,223 | B2 | 2/2008 | Wilson, Jr. |
| 7,329,266 | B2 | 2/2008 | Royse et al. |
| 7,331,968 | B2 | 2/2008 | Arp et al. |
| 7,338,503 | B2 | 3/2008 | Rosenberg et al. |
| 7,357,805 | B2 | 4/2008 | Masuda et al. |
| 7,510,562 | B2 | 3/2009 | Lindsay |
| 7,552,853 | B2 | 6/2009 | Mas et al. |
| 7,585,304 | B2 | 9/2009 | Hughett |
| 7,637,917 | B2 | 12/2009 | Whitfield et al. |
| 7,644,848 | B2 | 1/2010 | Swayze et al. |
| 7,686,820 | B2 | 3/2010 | Huitema et al. |
| 7,695,482 | B2 | 4/2010 | Viola |
| 7,717,926 | B2 | 5/2010 | Whitfield et al. |
| 7,727,248 | B2 | 6/2010 | Smith et al. |
| 7,731,724 | B2 | 6/2010 | Huitema et al. |
| 7,740,641 | B2 | 6/2010 | Huitema |
| 7,752,853 | B2 | 7/2010 | Singh et al. |
| 7,753,250 | B2 | 7/2010 | Clauson et al. |
| 7,766,207 | B2 | 8/2010 | Mather et al. |
| 7,819,886 | B2 | 10/2010 | Whitfield et al. |
| 7,887,553 | B2 | 2/2011 | Lehman et al. |
| 7,905,890 | B2 | 3/2011 | Whitfield et al. |
| 7,942,885 | B2 | 5/2011 | Sixto, Jr. et al. |
| 7,952,060 | B2 | 5/2011 | Watanabe et al. |
| 7,963,433 | B2 | 6/2011 | Whitman et al. |
| 7,988,027 | B2 | 8/2011 | Olson et al. |
| 8,011,550 | B2 | 9/2011 | Aranyi et al. |
| 8,011,555 | B2 | 9/2011 | Tarinelli et al. |
| 8,016,178 | B2 | 9/2011 | Olson et al. |
| 8,021,375 | B2 | 9/2011 | Aldrich et al. |
| 8,021,378 | B2 | 9/2011 | Sixto, Jr. et al. |
| 8,038,686 | B2 | 10/2011 | Huitema et al. |
| 8,048,088 | B2 | 11/2011 | Green et al. |
| 8,056,565 | B2 | 11/2011 | Zergiebel |
| 8,062,310 | B2 | 11/2011 | Shibata et al. |
| 8,066,720 | B2 | 11/2011 | Knodel et al. |
| 8,066,721 | B2 | 11/2011 | Kortenbach et al. |
| 8,066,722 | B2 | 11/2011 | Miyagi et al. |
| 8,070,760 | B2 | 12/2011 | Fujita |
| 8,075,571 | B2 | 12/2011 | Vitali et al. |
| 8,080,021 | B2 | 12/2011 | Griego |
| 8,083,668 | B2 | 12/2011 | Durgin et al. |
| 8,088,061 | B2 | 1/2012 | Wells et al. |
| 8,091,755 | B2 | 1/2012 | Kayan et al. |
| 8,100,926 | B1 | 1/2012 | Filshie et al. |
| 8,128,643 | B2 | 3/2012 | Aranyi et al. |
| 8,133,240 | B2 | 3/2012 | Damarati |
| 8,142,451 | B2 | 3/2012 | Boulnois et al. |
| 8,157,145 | B2 | 4/2012 | Shelton, IV et al. |
| 8,157,149 | B2 | 4/2012 | Olson et al. |
| 8,157,151 | B2 | 4/2012 | Ingmanson et al. |
| 8,172,859 | B2 | 5/2012 | Matsuno et al. |
| 8,172,870 | B2 | 5/2012 | Shipp |
| 8,187,290 | B2 | 5/2012 | Buckman et al. |
| 8,211,120 | B2 | 7/2012 | Itoh |

(56) References Cited

U.S. PATENT DOCUMENTS

| | | |
|---|---|---|
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,282,655 B2 | 10/2012 | Whitfield et al. |
| 8,308,743 B2 | 11/2012 | Matsuno et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,138 B2 | 3/2013 | Weisshaupt et al. |
| 8,403,945 B2 | 3/2013 | Whitfield et al. |
| 8,403,946 B2 | 3/2013 | Whitfield et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,717 B2 | 11/2013 | Sorrentino et al. |
| 8,603,109 B2 | 12/2013 | Aranyi et al. |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,814,884 B2 | 8/2014 | Whitfield et al. |
| 8,821,516 B2 | 9/2014 | Huitema |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,915,930 B2 | 12/2014 | Huitema et al. |
| 8,920,438 B2 | 12/2014 | Aranyi et al. |
| 8,939,974 B2 | 1/2015 | Boudreaux et al. |
| 8,950,646 B2 | 2/2015 | Viola |
| 8,961,542 B2 | 2/2015 | Whitfield et al. |
| 8,968,337 B2 | 3/2015 | Whitfield et al. |
| 8,973,804 B2 | 3/2015 | Hess et al. |
| 9,011,464 B2 | 4/2015 | Zammataro |
| 9,011,465 B2 | 4/2015 | Whitfield et al. |
| 9,089,334 B2 | 7/2015 | Sorrentino et al. |
| 9,113,892 B2 * | 8/2015 | Malkowski ........ A61B 17/1285 |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,282,961 B2 | 3/2016 | Whitman et al. |
| 9,282,972 B1 | 3/2016 | Patel et al. |
| 9,326,776 B2 | 5/2016 | Gadberry et al. |
| 9,358,011 B2 | 6/2016 | Sorrentino et al. |
| 9,358,015 B2 | 6/2016 | Sorrentino et al. |
| 9,364,216 B2 | 6/2016 | Rockrohr et al. |
| 9,364,239 B2 | 6/2016 | Malkowski |
| 9,364,240 B2 | 6/2016 | Whitfield et al. |
| 9,370,400 B2 | 6/2016 | Parihar |
| 9,393,024 B2 | 7/2016 | Whitfield et al. |
| 9,398,917 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,439,654 B2 | 9/2016 | Sorrentino et al. |
| 9,445,810 B2 | 9/2016 | Cappola |
| 9,480,477 B2 | 11/2016 | Aranyi et al. |
| 9,498,227 B2 | 11/2016 | Zergiebel et al. |
| 9,526,501 B2 | 12/2016 | Malkowski |
| 9,526,565 B2 | 12/2016 | Strobl |
| 9,532,787 B2 | 1/2017 | Zammataro |
| 9,545,254 B2 | 1/2017 | Sorrentino et al. |
| 9,549,741 B2 | 1/2017 | Zergiebel |
| 9,642,627 B2 | 5/2017 | Zammataro |
| 9,687,247 B2 | 6/2017 | Aranyi et al. |
| 9,717,504 B2 | 8/2017 | Huitema |
| 9,717,505 B2 | 8/2017 | Whitfield et al. |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,775,623 B2 | 10/2017 | Zammataro et al. |
| 9,775,624 B2 | 10/2017 | Rockrohr et al. |
| 9,782,181 B2 | 10/2017 | Vitali et al. |
| 9,848,886 B2 | 12/2017 | Malkowski et al. |
| 9,855,043 B2 | 1/2018 | Malkowski |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,136,939 B2 | 11/2018 | Minnelli et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 10,231,732 B1 | 3/2019 | Racenet et al. |
| 10,231,735 B2 | 3/2019 | Sorrentino et al. |
| 10,231,738 B2 | 3/2019 | Sorrentino et al. |
| 10,258,346 B2 | 4/2019 | Zergiebel et al. |
| 10,292,712 B2 | 5/2019 | Shankarsetty |
| 10,349,936 B2 | 7/2019 | Rockrohr et al. |
| 10,349,950 B2 | 7/2019 | Aranyi et al. |
| 10,357,250 B2 | 7/2019 | Zammataro |
| 10,363,045 B2 | 7/2019 | Whitfield et al. |
| 10,368,876 B2 | 8/2019 | Bhatnagar et al. |
| 10,390,831 B2 | 8/2019 | Holsten et al. |
| 10,426,489 B2 | 10/2019 | Baril |
| 2001/0047178 A1 | 11/2001 | Peters |
| 2002/0040226 A1 | 4/2002 | Laufer et al. |
| 2002/0068947 A1 | 6/2002 | Kuhns et al. |
| 2002/0082618 A1 | 6/2002 | Shipp et al. |
| 2002/0087169 A1 | 7/2002 | Brock et al. |
| 2002/0087170 A1 | 7/2002 | Kuhns et al. |
| 2002/0099388 A1 | 7/2002 | Mayenberger |
| 2002/0120279 A1 | 8/2002 | Deguillebon et al. |
| 2002/0123742 A1 | 9/2002 | Baxter et al. |
| 2002/0128668 A1 | 9/2002 | Manetakis et al. |
| 2002/0177859 A1 | 11/2002 | Monassevitch et al. |
| 2002/0198537 A1 | 12/2002 | Smith et al. |
| 2002/0198538 A1 | 12/2002 | Kortenbach et al. |
| 2002/0198539 A1 | 12/2002 | Sixto et al. |
| 2002/0198540 A1 | 12/2002 | Smith et al. |
| 2002/0198541 A1 | 12/2002 | Smith et al. |

(56) References Cited

U.S. PATENT DOCUMENTS

| | | |
|---|---|---|
| 2003/0014060 A1 | 1/2003 | Wilson et al. |
| 2003/0018345 A1 | 1/2003 | Green |
| 2003/0023249 A1 | 1/2003 | Manetakis |
| 2003/0040759 A1 | 2/2003 | de Guillebon et al. |
| 2003/0105476 A1 | 6/2003 | Sancoff et al. |
| 2003/0114867 A1 | 6/2003 | Bolduc et al. |
| 2003/0135224 A1 | 7/2003 | Blake |
| 2003/0167063 A1 | 9/2003 | Kerr |
| 2003/0208231 A1 | 11/2003 | Williamson et al. |
| 2003/0220657 A1 | 11/2003 | Adams |
| 2003/0225423 A1 | 12/2003 | Huitema |
| 2003/0229360 A1 | 12/2003 | Gayton |
| 2003/0233105 A1 | 12/2003 | Gayton |
| 2004/0010272 A1 | 1/2004 | Manetakis et al. |
| 2004/0044352 A1 | 3/2004 | Fowler et al. |
| 2004/0097970 A1 | 5/2004 | Hughett |
| 2004/0097971 A1 | 5/2004 | Hughett |
| 2004/0097972 A1 | 5/2004 | Shipp et al. |
| 2004/0106936 A1 | 6/2004 | Shipp et al. |
| 2004/0133215 A1 | 7/2004 | Baxter |
| 2004/0138681 A1 | 7/2004 | Pier |
| 2004/0153100 A1 | 8/2004 | Ahlberg et al. |
| 2004/0158266 A1 | 8/2004 | Damarati |
| 2004/0162567 A9 | 8/2004 | Adams |
| 2004/0167545 A1 | 8/2004 | Sadler et al. |
| 2004/0176776 A1 | 9/2004 | Zubok et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0080440 A1 | 4/2005 | Durgin et al. |
| 2005/0090837 A1 | 4/2005 | Sixto et al. |
| 2005/0090838 A1 | 4/2005 | Sixto et al. |
| 2005/0096670 A1 | 5/2005 | Wellman et al. |
| 2005/0096671 A1 | 5/2005 | Wellman et al. |
| 2005/0096672 A1 | 5/2005 | Manetakis et al. |
| 2005/0101975 A1 | 5/2005 | Nguyen et al. |
| 2005/0107807 A1 | 5/2005 | Nakao |
| 2005/0107809 A1 | 5/2005 | Litscher et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0113847 A1 | 5/2005 | Gadberry et al. |
| 2005/0119671 A1 | 6/2005 | Reydel et al. |
| 2005/0119673 A1 | 6/2005 | Gordon et al. |
| 2005/0119677 A1 | 6/2005 | Shipp |
| 2005/0125010 A1 | 6/2005 | Smith et al. |
| 2005/0143767 A1 | 6/2005 | Kimura et al. |
| 2005/0149063 A1 | 7/2005 | Young et al. |
| 2005/0149064 A1 | 7/2005 | Peterson et al. |
| 2005/0149068 A1 | 7/2005 | Williams et al. |
| 2005/0149069 A1 | 7/2005 | Bertolero et al. |
| 2005/0165415 A1 | 7/2005 | Wales |
| 2005/0165418 A1 | 7/2005 | Chan |
| 2005/0171560 A1 | 8/2005 | Hughett |
| 2005/0175703 A1 | 8/2005 | Hunter et al. |
| 2005/0177176 A1 | 8/2005 | Gerbi et al. |
| 2005/0203547 A1 | 9/2005 | Weller et al. |
| 2005/0203548 A1 | 9/2005 | Weller et al. |
| 2005/0216036 A1 | 9/2005 | Nakao |
| 2005/0216056 A1 | 9/2005 | Valdevit et al. |
| 2005/0222588 A1 | 10/2005 | Vandenbroek et al. |
| 2005/0222590 A1 | 10/2005 | Gadberry et al. |
| 2005/0222665 A1 | 10/2005 | Aranyi |
| 2005/0228411 A1 | 10/2005 | Manzo |
| 2005/0228416 A1 | 10/2005 | Burbank et al. |
| 2005/0234478 A1 | 10/2005 | Wixey et al. |
| 2005/0251183 A1 | 11/2005 | Buckman et al. |
| 2005/0251184 A1 | 11/2005 | Anderson |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2005/0288690 A1 | 12/2005 | Bourque et al. |
| 2006/0000867 A1 | 1/2006 | Shelton et al. |
| 2006/0004388 A1 | 1/2006 | Whayne et al. |
| 2006/0004390 A1 | 1/2006 | Rosenberg et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079115 A1 | 4/2006 | Aranyi |
| 2006/0079913 A1 | 4/2006 | Whitfield et al. |
| 2006/0085021 A1 | 4/2006 | Wenzler |
| 2006/0100649 A1 | 5/2006 | Hart |
| 2006/0111731 A1 | 5/2006 | Manzo |
| 2006/0124485 A1 | 6/2006 | Kennedy |
| 2006/0129170 A1 | 6/2006 | Royce et al. |
| 2006/0135992 A1 | 6/2006 | Bettuchi et al. |
| 2006/0163312 A1 | 7/2006 | Viola et al. |
| 2006/0173470 A1 | 8/2006 | Oray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker et al. |
| 2006/0212050 A1 | 9/2006 | D'Agostino et al. |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0241655 A1 | 10/2006 | Viola |
| 2006/0259045 A1 | 11/2006 | Damarati |
| 2006/0259049 A1 | 11/2006 | Harada et al. |
| 2006/0264987 A1 | 11/2006 | Sgro |
| 2006/0271072 A1 | 11/2006 | Hummel et al. |
| 2007/0016228 A1 | 1/2007 | Salas |
| 2007/0021761 A1 | 1/2007 | Phillips |
| 2007/0021766 A1 | 1/2007 | Belagali et al. |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | de la Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |
| 2007/0066981 A1 | 3/2007 | Meagher |
| 2007/0073314 A1 | 3/2007 | Gadberry et al. |
| 2007/0083218 A1 | 4/2007 | Morris |
| 2007/0093790 A1 | 4/2007 | Downey et al. |
| 2007/0106314 A1 | 5/2007 | Dunn |
| 2007/0112365 A1 | 5/2007 | Hilal et al. |
| 2007/0118155 A1 | 5/2007 | Goldfarb et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier et al. |
| 2007/0142848 A1 | 6/2007 | Ainsworth et al. |
| 2007/0142851 A1 | 6/2007 | Sixto et al. |
| 2007/0149988 A1 | 6/2007 | Michler et al. |
| 2007/0149989 A1 | 6/2007 | Santilli et al. |

(56) References Cited

U.S. PATENT DOCUMENTS

| | | |
|---|---|---|
| 2007/0162060 A1 | 7/2007 | Wild |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203509 A1 | 8/2007 | Bettuchi |
| 2007/0203510 A1 | 8/2007 | Bettuchi |
| 2007/0213747 A1 | 9/2007 | Monassevitch et al. |
| 2007/0250080 A1 | 10/2007 | Jones et al. |
| 2007/0265640 A1 | 11/2007 | Kortenbach et al. |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0004636 A1 | 1/2008 | Walberg et al. |
| 2008/0004637 A1 | 1/2008 | Klassen et al. |
| 2008/0004639 A1 | 1/2008 | Huitema et al. |
| 2008/0015615 A1 | 1/2008 | Molitor et al. |
| 2008/0027465 A1 | 1/2008 | Vitali et al. |
| 2008/0027466 A1 | 1/2008 | Vitali et al. |
| 2008/0045981 A1 | 2/2008 | Margolin et al. |
| 2008/0051808 A1 | 2/2008 | Rivera et al. |
| 2008/0065118 A1 | 3/2008 | Damarati |
| 2008/0083813 A1 | 4/2008 | Zemlok et al. |
| 2008/0103510 A1 | 5/2008 | Taylor et al. |
| 2008/0140090 A1 | 6/2008 | Aranyi et al. |
| 2008/0147092 A1 | 6/2008 | Rogge et al. |
| 2008/0147093 A1 | 6/2008 | Roskopf et al. |
| 2008/0154287 A1 | 6/2008 | Rosenberg et al. |
| 2008/0167665 A1 | 7/2008 | Arp et al. |
| 2008/0228199 A1 | 9/2008 | Cropper et al. |
| 2008/0243145 A1 | 10/2008 | Whitfield et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312665 A1 | 12/2008 | Shibata et al. |
| 2008/0319456 A1 | 12/2008 | Hart |
| 2009/0076533 A1 | 3/2009 | Kayan et al. |
| 2009/0088777 A1 | 4/2009 | Miyagi et al. |
| 2009/0088783 A1 | 4/2009 | Kennedy et al. |
| 2009/0171380 A1 | 7/2009 | Whiting |
| 2009/0204115 A1 | 8/2009 | Dees, Jr. et al. |
| 2009/0209946 A1 | 8/2009 | Swayze et al. |
| 2009/0222003 A1 | 9/2009 | Otley |
| 2009/0228023 A1 | 9/2009 | Cui |
| 2009/0228024 A1 | 9/2009 | Whitfield et al. |
| 2009/0261142 A1 | 10/2009 | Milliman et al. |
| 2009/0264904 A1 | 10/2009 | Aldrich et al. |
| 2009/0299382 A1 | 12/2009 | Zergiebel |
| 2009/0312775 A1 | 12/2009 | Gilkey et al. |
| 2009/0326558 A1 | 12/2009 | Cui et al. |
| 2010/0049216 A1 | 2/2010 | Zergiebel |
| 2010/0057105 A1 | 3/2010 | Sorrentino et al. |
| 2010/0057107 A1 | 3/2010 | Sorrentino et al. |
| 2010/0089970 A1 | 4/2010 | Smith et al. |
| 2010/0137886 A1 | 6/2010 | Zergiebel et al. |
| 2010/0274262 A1 | 10/2010 | Schulz et al. |
| 2010/0274264 A1 | 10/2010 | Schulz et al. |
| 2010/0318103 A1 | 12/2010 | Cheng et al. |
| 2010/0331862 A1 | 12/2010 | Monassevitch et al. |
| 2011/0054498 A1 | 3/2011 | Monassevitch et al. |
| 2011/0082474 A1 | 4/2011 | Bindra et al. |
| 2011/0087220 A1 | 4/2011 | Felder et al. |
| 2011/0087241 A1 | 4/2011 | Nguyen |
| 2011/0087243 A1 | 4/2011 | Nguyen et al. |
| 2011/0087268 A1 | 4/2011 | Livneh |
| 2011/0112552 A1 | 5/2011 | Lehman et al. |
| 2011/0137323 A1 | 6/2011 | Malkowski et al. |
| 2011/0137324 A1 | 6/2011 | Boudreaux et al. |
| 2011/0144662 A1 | 6/2011 | McLawhorn et al. |
| 2011/0144665 A1 | 6/2011 | Malkowski |
| 2011/0190791 A1 | 8/2011 | Jacobs et al. |
| 2011/0208211 A1 | 8/2011 | Whitfield et al. |
| 2011/0208212 A1 | 8/2011 | Zergiebel et al. |
| 2011/0218553 A1 | 9/2011 | Huitema et al. |
| 2011/0218554 A1 | 9/2011 | Cheng et al. |
| 2011/0218555 A1 | 9/2011 | Huitema |
| 2011/0218556 A1 | 9/2011 | Nguyen et al. |
| 2011/0224696 A1 | 9/2011 | Huitema et al. |
| 2011/0224700 A1 | 9/2011 | Schmidt et al. |
| 2011/0224701 A1 | 9/2011 | Menn |
| 2011/0230900 A1 | 9/2011 | Sarradon |
| 2011/0245847 A1 | 10/2011 | Menn et al. |
| 2011/0245848 A1 | 10/2011 | Rosenberg et al. |
| 2011/0295290 A1 | 12/2011 | Whitfield |
| 2011/0313437 A1 | 12/2011 | Yeh |
| 2012/0022526 A1 | 1/2012 | Aldridge et al. |
| 2012/0029534 A1 | 2/2012 | Whitfield et al. |
| 2012/0041455 A1 | 2/2012 | Martinez |
| 2012/0046671 A1 | 2/2012 | Matsuoka et al. |
| 2012/0053402 A1 | 3/2012 | Conlon et al. |
| 2012/0059394 A1 | 3/2012 | Brenner et al. |
| 2012/0065647 A1 | 3/2012 | Litscher et al. |
| 2012/0109158 A1 | 5/2012 | Zammataro |
| 2012/0116420 A1 | 5/2012 | Sorrentino et al. |
| 2012/0197269 A1 | 8/2012 | Zammataro |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0277765 A1 | 11/2012 | Zammataro et al. |
| 2012/0330326 A1 | 12/2012 | Creston et al. |
| 2013/0041379 A1 | 2/2013 | Bodor et al. |
| 2013/0110135 A1 | 5/2013 | Whitfield et al. |
| 2013/0131697 A1 | 5/2013 | Hartoumbekis |
| 2013/0165951 A1 | 6/2013 | Blake, III |
| 2013/0165952 A1 | 6/2013 | Whitfield et al. |
| 2013/0172909 A1 | 7/2013 | Harris |
| 2013/0172910 A1 | 7/2013 | Malkowski |
| 2013/0172911 A1 | 7/2013 | Rockrohr et al. |
| 2013/0172912 A1 | 7/2013 | Whitfield et al. |
| 2013/0175320 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2013/0253541 A1 | 9/2013 | Zergiebel |
| 2013/0274767 A1 | 10/2013 | Sorrentino et al. |
| 2013/0289583 A1 | 10/2013 | Zergiebel et al. |
| 2013/0296891 A1 | 11/2013 | Hartoumbekis |
| 2013/0296892 A1 | 11/2013 | Sorrentino et al. |
| 2013/0310849 A1 | 11/2013 | Malkowski |
| 2013/0325040 A1 | 12/2013 | Zammataro |
| 2013/0325057 A1 | 12/2013 | Larson et al. |
| 2014/0005693 A1 | 1/2014 | Shelton, IV et al. |
| 2014/0005696 A1* | 1/2014 | Schulz ............... A61B 17/1285 606/143 |
| 2014/0012291 A1* | 1/2014 | Ahlberg ............... A61B 17/128 606/143 |
| 2014/0039526 A1 | 2/2014 | Malkowski |
| 2014/0052157 A1 | 2/2014 | Whitfield et al. |
| 2014/0058412 A1 | 2/2014 | Aranyi et al. |
| 2014/0074143 A1 | 3/2014 | Fitzgerald et al. |
| 2014/0188159 A1 | 7/2014 | Steege |
| 2014/0194903 A1 | 7/2014 | Malkowski et al. |
| 2014/0207156 A1 | 7/2014 | Malkowski |
| 2014/0263565 A1 | 9/2014 | Lytle, IV et al. |
| 2014/0276970 A1 | 9/2014 | Messerly et al. |
| 2014/0296879 A1 | 10/2014 | Menn et al. |
| 2014/0316441 A1 | 10/2014 | Zergiebel et al. |
| 2014/0330291 A1 | 11/2014 | Whitfield et al. |
| 2014/0371728 A1 | 12/2014 | Vaughn |
| 2015/0005790 A1 | 1/2015 | Whitfield et al. |
| 2015/0032131 A1 | 1/2015 | Sorrentino et al. |
| 2015/0066057 A1 | 3/2015 | Rockrohr et al. |
| 2015/0080916 A1 | 3/2015 | Aranyi et al. |
| 2015/0127022 A1 | 5/2015 | Whitfield et al. |
| 2015/0201953 A1 | 7/2015 | Strobl et al. |
| 2015/0265282 A1 | 9/2015 | Miles et al. |
| 2015/0313452 A1 | 11/2015 | Hasser et al. |
| 2015/0314451 A1 | 11/2015 | Nixon |
| 2016/0004956 A1 | 1/2016 | Reynolds et al. |
| 2016/0030044 A1 | 2/2016 | Zammataro |
| 2016/0030045 A1 | 2/2016 | Malkowski et al. |
| 2016/0113655 A1 | 4/2016 | Holsten |
| 2016/0151071 A1 | 6/2016 | Tokarz et al. |
| 2016/0192940 A1 | 7/2016 | Gokharu |
| 2016/0213377 A1 | 7/2016 | Shankarsetty |

(56) References Cited

U.S. PATENT DOCUMENTS

| | | |
|---|---|---|
| 2016/0242789 A1 | 8/2016 | Sorrentino et al. |
| 2016/0256157 A1 | 9/2016 | Rockrohr et al. |
| 2016/0256158 A1 | 9/2016 | Whitfield et al. |
| 2016/0262764 A1 | 9/2016 | Gokharu |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Aravalli |
| 2017/0202567 A1 | 7/2017 | Griffiths et al. |
| 2017/0238936 A1 | 8/2017 | Mujawar |
| 2017/0245921 A1 | 8/2017 | Joseph et al. |
| 2017/0252042 A1 | 9/2017 | Kethman et al. |
| 2017/0258472 A1 | 9/2017 | Aranyi et al. |
| 2017/0290587 A1 | 10/2017 | Schober et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0021041 A1 | 1/2018 | Zhang et al. |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |
| 2019/0021738 A1 | 1/2019 | Hartoumbekis |
| 2019/0038375 A1 | 2/2019 | Baril et al. |
| 2019/0046202 A1 | 2/2019 | Baril et al. |
| 2019/0046203 A1 | 2/2019 | Baril et al. |
| 2019/0046207 A1 | 2/2019 | Czemik et al. |
| 2019/0046208 A1 | 2/2019 | Baril et al. |
| 2019/0053806 A1 | 2/2019 | Zhang et al. |
| 2019/0053808 A1 | 2/2019 | Baril et al. |
| 2019/0059904 A1 | 2/2019 | Zammataro |
| 2019/0076147 A1 | 3/2019 | Baril et al. |
| 2019/0076148 A1 | 3/2019 | Baril et al. |
| 2019/0076149 A1 | 3/2019 | Baril et al. |
| 2019/0076150 A1 | 3/2019 | Gokharu |
| 2019/0076210 A1 | 3/2019 | Baril et al. |
| 2019/0133583 A1 | 5/2019 | Baril et al. |
| 2019/0133584 A1 | 5/2019 | Baril et al. |
| 2019/0133593 A1 | 5/2019 | P V R |
| 2019/0133594 A1 | 5/2019 | Dinino et al. |
| 2019/0133595 A1 | 5/2019 | Baril et al. |
| 2019/0150935 A1 | 5/2019 | Raikar et al. |
| 2019/0175176 A1 | 6/2019 | Zammataro |
| 2019/0175187 A1 | 6/2019 | P V R |
| 2019/0175188 A1 | 6/2019 | P V R |
| 2019/0175189 A1 | 6/2019 | P V R |
| 2019/0192139 A1 | 6/2019 | Rockrohr et al. |
| 2019/0209177 A1 | 7/2019 | Whitfield et al. |
| 2019/0216464 A1 | 7/2019 | Baril et al. |
| 2019/0239893 A1 | 8/2019 | Shankarsetty |

FOREIGN PATENT DOCUMENTS

| | | |
|---|---|---|
| CA | 1163889 | 3/1984 |
| CA | 2740831 A1 | 4/2010 |
| CN | 1994236 A | 7/2007 |
| CN | 101401737 A | 4/2009 |
| CN | 101530340 A | 9/2009 |
| CN | 100571640 C | 12/2009 |
| CN | 101658437 A | 3/2010 |
| CN | 101664329 A | 3/2010 |
| CN | 101664331 A | 3/2010 |
| CN | 201683954 U | 12/2010 |
| CN | 102342853 A | 2/2012 |
| CN | 103083059 A | 5/2013 |
| CN | 103181809 A | 7/2013 |
| CN | 103181810 A | 7/2013 |
| CN | 103251441 A | 8/2013 |
| CN | 104487006 A | 4/2015 |
| CN | 104605911 B | 2/2017 |
| DE | 202007003398 U1 | 6/2007 |
| EP | 0073655 A1 | 3/1983 |
| EP | 0086721 A2 | 8/1983 |
| EP | 0089737 A1 | 9/1983 |
| EP | 0092300 A1 | 10/1983 |
| EP | 0324166 A2 | 7/1989 |
| EP | 0392750 A1 | 10/1990 |
| EP | 0409569 A1 | 1/1991 |
| EP | 0569223 A1 | 11/1993 |
| EP | 0594003 A1 | 4/1994 |
| EP | 0598529 A2 | 5/1994 |
| EP | 0622049 A1 | 11/1994 |
| EP | 0685204 A1 | 12/1995 |
| EP | 0732078 A2 | 9/1996 |
| EP | 0755655 A2 | 1/1997 |
| EP | 0760230 A1 | 3/1997 |
| EP | 0769274 A1 | 4/1997 |
| EP | 0769275 A1 | 4/1997 |
| EP | 0834286 A1 | 4/1998 |
| EP | 1317906 A1 | 6/2003 |
| EP | 1468653 A2 | 10/2004 |
| EP | 1609427 A1 | 12/2005 |
| EP | 1712187 A2 | 10/2006 |
| EP | 1712191 A2 | 10/2006 |
| EP | 1757236 A2 | 2/2007 |
| EP | 1813199 A1 | 8/2007 |
| EP | 1813207 A1 | 8/2007 |
| EP | 1894531 A2 | 3/2008 |
| EP | 1908423 A2 | 4/2008 |
| EP | 1913881 A1 | 4/2008 |
| EP | 1939231 A1 | 7/2008 |
| EP | 2000102 A2 | 12/2008 |
| EP | 2140817 A1 | 1/2010 |
| EP | 2229895 A1 | 9/2010 |
| EP | 2 263 570 A1 | 12/2010 |
| EP | 2332471 A1 | 6/2011 |
| EP | 2412318 A2 | 2/2012 |
| EP | 2412319 A2 | 2/2012 |
| EP | 2 752 165 A2 | 7/2014 |
| EP | 3132756 A1 | 2/2017 |
| GB | 1134832 A | 11/1968 |
| GB | 2073022 A | 10/1981 |
| GB | 2 132 899 A | 7/1984 |
| JP | 10118083 | 5/1998 |
| JP | 2003033361 A | 2/2003 |
| JP | 2006501954 A | 1/2006 |
| JP | 2006154230 A | 6/2006 |
| JP | 2006209948 A | 8/2006 |
| JP | 2006277221 A | 10/2006 |
| JP | 2007250843 A | 9/2007 |
| JP | 2008017876 A | 1/2008 |
| JP | 2008055165 A | 3/2008 |
| JP | 2008515550 A | 5/2008 |
| JP | 2009198991 A | 9/2009 |

(56) References Cited

FOREIGN PATENT DOCUMENTS

| | | |
|---|---|---|
| JP | 2011186812 A | 9/2011 |
| JP | 2013166982 A | 8/2013 |
| JP | 5499386 B2 | 5/2014 |
| WO | 9003763 A1 | 4/1990 |
| WO | 0042922 A1 | 7/2000 |
| WO | 01/65997 A2 | 9/2001 |
| WO | 2001-66001 A2 | 9/2001 |
| WO | 2001-67965 A1 | 9/2001 |
| WO | 2003-086207 A1 | 10/2003 |
| WO | 2003-092473 A2 | 11/2003 |
| WO | 2004032762 A1 | 4/2004 |
| WO | 2005091457 A1 | 9/2005 |
| WO | 2006042076 A2 | 4/2006 |
| WO | 2006042084 A2 | 4/2006 |
| WO | 2006042110 A2 | 4/2006 |
| WO | 2006042141 A2 | 4/2006 |
| WO | 2006135479 A2 | 12/2006 |
| WO | 2008118928 A2 | 10/2008 |
| WO | 2008127968 A2 | 10/2008 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |
| WO | 2017084000 A1 | 5/2017 |
| WO | 2017146138 A1 | 8/2017 |

OTHER PUBLICATIONS

The Extended European Search Report corresponding to EP 11 25 0194.5, completed Nov. 25, 2013 and dated Dec. 3, 2013; (8 Pages).
The Extended European Search Report corresponding to EP 10 25 1798.4, completed Dec. 12, 2013 and dated Jan. 2, 2014; (9 Pages).
"Salute II Disposable Fixation Device", Technique Guide—Laparoscopic and Open Inguinal and Ventral Hernia Repair; Davol, A Bard Company, 2006; (7 Pages).
The Extended European Search Report corresponding to EP 10 25 2112.7, completed Jul. 29, 2014 and dated Aug. 5, 2014; (8 pp).
The Extended European Search Report corresponding to EP 14 15 1673.2, completed Apr. 25, 2014 and dated May 8, 2014; (8 pp).
Chinese First Office Action corresponding to counterpart Int'l Appln. No. CN 201210586826.1 dated Dec. 30, 2015.
Extended European Search Report corresponding to counterpart Int'l Appln. No. EP 15 19 1313.4 dated Feb. 1, 2016.
Extended European Search Report corresponding to counterpart Int'l Appln. No. EP 15 18 5362.9 dated Feb. 12, 2016.
Extended European Search Report corresponding to counterpart Int'l Appln. No. EP 12 19 7813.4 dated Mar. 7, 2016.
Canadian Office Action corresponding to counterpart Int'l Appln. No. CA 2,676,465 dated Mar. 8, 2016.
Japanese Office Action corresponding to counterpart Int'l Appln. No. JP 2014-245081 dated Mar. 18, 2016.
Japanese Office Action corresponding to counterpart Int'l Appln. No. JP 2015-005629 dated Mar. 18, 2016.
Extended European Search Report corresponding to counterpart Int'l Appln. No. EP 15 19 3549.1 dated Mar. 22, 2016,.
International Search Report and Written Opinion corresponding to counterpart Int'l Appln. No. PCT/CN2015/082199 dated Mar. 31, 2016.
Extended European Search Report corresponding to counterpart Int'l Appln. No. EP 15 19 7251.0 dated Apr. 8, 2016.
Extended European Search Report corresponding to counterpart Int'l Appln. No. EP 16 15 0739.7 dated May 17, 2016.
Canadian Office Action corresponding to counterpart Int'l Appln. No. CA 2,716,672 dated May 31, 2016.
Canadian Office Action corresponding to counterpart Int'l Appln. No. CA 2,717,448 dated May 31, 2016.
Canadian Office Action corresponding to counterpart Int'l Appln. No. CA 2,721,951 dated Jun. 1, 2016.
Partial European Search Report corresponding to counterpart Int'l Appln. No. EP 16 15 0287.7 dated Jun. 16, 2016.
Chinese Second Office Action corresponding to counterpart Int'l Appln. No. CN 201210555570.8 dated Jun. 20, 2016.
International Search Report & Written Opinion corresponding to Int'l Appln. No. PCT/CN2015/091603 dated Jul. 8, 2016.
Chinese Second Office Action corresponding to Int'l Appln. No. CN 201210586814.9 dated Jul. 18, 2016.
Chinese First Office Action corresponding to Int'l Appln. No. CN 201510093591.6 dated Jul. 25, 2016.
International Search Report & Written Opinion corresponding to Int'l Appln. No. PCT/CN2015/094172 dated Aug. 4, 2016.
Canadian Office Action corresponding to Int'l Appln. No. CA 2,728,538 dated Sep. 6, 2016.
Chinese Second Office Action corresponding to Int'l Appln. No. CN 201210586826.1 dated Sep. 14, 2016.
Extended European Search Report corresponding to Int'l Appln. No. EP 16 15 0287.7 dated Oct. 4, 2016.
Chinese First Office Action corresponding to Int'l Appln. No. CN 201510205737.1 dated Nov. 1, 2016.
European Office Action corresponding to Int'l Appln. No. EP 08 73 2820.9 dated Nov. 3, 2016.
Extended European Search Report corresponding to Int'l Appln. No. EP 16 18 5465.8 dated Dec. 21, 2016.
Extended European Search Report corresponding to Int'l Appln. No. EP 16 18 4652.2 dated Jan. 4, 2017.
Chinese First Office Action corresponding to Int'l Appln. No. CN 201510419902.3 dated Jan. 4, 2017.
Extended European Search Report corresponding to counterpart Int'l Appln. No. EP 17 15 3714.5 dated May 11, 2017.
Extended European Search Report corresponding to Patent Application EP 18154617.7 dated Jun. 25, 2018.
Extended European Search Report corresponding to Patent Application EP 18155158.1 dated Jun. 28, 2018.
Extended European Search Report corresponding to Patent Application EP 15877428.1 dated Jul. 2, 2018.
Extended European Search Report corresponding to Patent Application EP 18157789.1 dated Jul. 5, 2018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.
Extended European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.
Japanese Office Action corresponding to JP 2011-160130 dated Dec. 1, 2014.
Chinese Office Action corresponding to CN 201210015011.8 dated Jan. 4, 2015.
Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.

(56) References Cited

OTHER PUBLICATIONS

Extended European Search Report corresponding to EP 14 16 1540.1 dated Feb. 27, 2015.
Australian Office Action corresponding to AU 2010226985 dated Mar. 31, 2015.
Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.
European Office Action corresponding to EP 12 152 989.5 dated May 4, 2015.
Australian Office Action corresponding to AU 2009212759 dated May 7, 2015.
Japanese Office Action corresponding to JP 2013-229070 dated May 8, 2015.
Japanese Office Action corresponding to JP 2013-229996 dated May 8, 2015.
Japanese Office Action corresponding to JP 2014-190735 dated May 27, 2015; no English translation attached—unavailable.
Extended European Search Report corresponding to EP 14 18 2236.1, completed Jan. 9, 2105 and dated Jan. 20, 2015; (9 pp).
The extended European Search Report corresponding to European Application No. EP 07 25 3905.9, completed Jan. 29, 2008; dated Feb. 7, 2008; (7 Pages).
International Search Report corresponding to International Application No. PCT-US08-58185, completed Sep. 4, 2008; dated Sep. 9, 2008; (2 Pages).
The International Search Report corresponding to International Application No. PCT-US08-59859, completed Sep. 14, 2008; dated Sep. 18, 2008; (2 Pages).
The extended European Search Report corresponding to European Application No. EP 07 25 3807.7, completed Nov. 7, 2008; dated Nov. 26, 2008; (11 Pages).
The extended European Search Report corresponding to European Application No. EP 09 25 2049.3, completed Dec. 11, 2009; dated Jan. 12, 2010; (3 Pages).
The extended European Search Report corresponding to European Application No. EP 09 25 2050.1, completed Dec. 23, 2009; dated Jan. 21, 2010; (3 Pages).
The extended European Search Report corresponding to European Application No. EP 09 25 2051.9, completed Dec. 21, 2009; dated Jan. 28, 2010; (3 Pages).
The extended European Search Report corresponding to European Application No. EP 09 25 2052.7, completed Nov. 16, 2009; dated Nov. 24, 2009; (3 Pages).
The extended European Search Report corresponding to European Application No. EP 09 25 2053.5, completed Nov. 24, 2009; dated Dec. 1, 2009; (3 Pages).
The extended European Search Report corresponding to European Application No. EP 09 25 2054.3, completed Jan. 7, 2010; dated Jan. 22, 2010; (3 Pages).
The extended European Search Report corresponding to European Application No. EP 09 25 2056.8, completed Jan. 8, 2010; dated Feb. 5, 2010; (3 Pages).
The extended European Search Report corresponding to European Application No. EP 10 25 0497.4, completed May 4, 2010; dated May 12, 2010; (6 Pages).
The extended European Search Report corresponding to European Application No. EP 10 25 2079.8, completed Mar. 8, 2011; dated Mar. 17, 2011; (3 Pages).
The European Search Report corresponding to European Application No. EP 05 81 0218.7, completed Apr. 18, 2011; dated May 20, 2011; (3 pages).
The European Search Report corresponding to European Application No. EP 05 80 7612.6, completed May 2, 2011; dated May 20, 2011; (3 pages).
The extended European Search Report corresponding to European Application No. EP 10 25 1737.2, completed May 9, 2011; dated May 20, 2011; (4 pages).
The extended European Search Report corresponding to European Application No. EP 11 25 0214.1, completed May 25, 2011; dated Jun. 1, 2011; (3 Pages).
The extended European Search Report corresponding to European Application No. EP 11 00 2681.2, completed May 31, 2011; dated Jun. 10, 2011; (3 Pages).
The European Search Report corresponding to European Application No. EP 05 80 2686.5, completed Jan. 9, 2012; dated Jan. 18, 2012; (3 Pages).
The extended European Search Report corresponding to European Application No. Ep 12 15 1313.9, completed Mar. 20, 2012 and dated Apr. 12, 2012; (5 Pages).
The extended European Search Report corresponding to European Application No. EP 12 16 1291.5, completed Apr. 24, 2012 and dated May 4, 2012; (5 Pages).
The extended European Search Report corresponding to European Application No. EP 12 16 5891.8, completed Jun. 12, 2012 and dated Jun. 20, 2012; (6 Pages).
The extended European Search Report corresponding to European Application No. EP 12 16 2288.0, completed Jun. 4, 2012 and dated Jul. 7, 2012; (6 Pages).
The extended European Search Report corresponding to European Application No. EP 12 16 4955.2, completed Aug. 23, 2012 and dated Sep. 4, 2012; (5 Pages).
The extended European Search Report corresponding to European Application No. EP 11 25 0754.6, completed Oct. 22, 2012 and dated Oct. 31, 2012; (6 Pages).
The extended European Search Report corresponding to European Application No. EP 12 18 6401.1, completed Nov. 22, 2012 and dated Nov. 30, 2012; (7 Pages).
The extended European Search Report corresponding to European Application No. EP 12 18 6448.2, completed Nov. 28, 2012 and dated Dec. 10, 2012; (6 Pages).
The extended European Search Report corresponding to European Application No. EP 12 19 1706.6, completed Dec. 19, 2012 and dated Jan. 8, 2013; (6 Pages).
The Extended European Search Report corresponding to EP 12 19 8745.7, completed Mar. 19, 2013 and dated Apr. 11, 2013; (8 Pages).
The Extended European Search Report corresponding to EP 12 15 2989.5, completed Apr. 9, 2013 and dated Apr. 18, 2013; (9 Pages).
The Extended European Search Report corresponding to EP 08 73 2820.9, completed Jul. 2, 2013 and dated Jul. 9, 2013; (10 Pages).
The Extended European Search Report corresponding to EP 13 17 2008.8, completed Aug. 14, 2013 and dated Aug. 28, 2013; (8 Pages).
Chinese First Office Action corresponding to counterpart Chinese Patent Application No. CN 2014104295806 dated Aug. 31, 2017.
European Office Action corresponding to European Appln. No. EP 16 15 9324.9 dated Aug. 7, 2017.
Chinese First Office Action corresponding to Chinese Appln. No. CN 2014104295806 dated Aug. 31, 2017.
Extended European Search Report corresponding to European Appln. No. EP 17 17 3508.7 dated Sep. 29, 2017.
Chinese Second Office Action corresponding to Chinese Appln. No. CN 201410076318.8 dated Oct. 10, 2017.
Extended European Search Report corresponding to European Appln. No. EP 17 18 0570.8 dated Dec. 6, 2017.
International Search Report corresponding to Int'l Patent Appln. PCT/US2018/050316 dated Dec. 31, 2018.
International Search Report corresponding to Int'l Patent Appln. PCT/US2018/050336 dated Jan. 7, 2019.
International Search Report corresponding to Int'l Patent Appln. PCT/US2018/050325 dated Jan. 7, 2019.
International Search Report corresponding to Int'l Patent Appln. PCT/US2018/045306 dated Jan. 16, 2019.
International Search Report corresponding to Int'l Patent Appln. PCT/US2018/050349 dated Jan. 21, 2019.
International Search Report corresponding to Int'l Patent Appln. PCT/US2018/045725 dated Jan. 28, 2019.

(56) References Cited

OTHER PUBLICATIONS

Extended European Search Report corresponding to European Patent Application EP 18208630.6 dated Feb. 12, 2019.
International Search Report corresponding to Int'l Patent Appln. PCT/US2018/057910 dated Feb. 22, 2019.
International Search Report corresponding to Int'l Patent Appln. PCT/US2018/057922 dated Feb. 22, 2019.
International Search Report corresponding to Int'l Patent Appln. PCT/US2018/058078 dated Feb. 22, 2019.
International Search Report corresponding to Int'l Patent Appln. PCT/US2018/058603 dated Feb. 22, 2019.
International Search Report corresponding to Int'l Patent Appln. PCT/US2018/057221 dated Mar. 11, 2019.
Extended European Search Report corresponding to European Patent Application EP 18212043.6 dated Apr. 24, 2019.
Extended European Search Report corresponding to European Patent Application EP 18211565.9 dated Apr. 26, 2019.
Extended European Search Report corresponding to European Patent Application EP 18211921.4 dated Apr. 30, 2019.
Chinese First Office Action corresponding to Chinese Patent Application CN 201510868226.8 dated May 29, 2019.
Extended European Search Report corresponding to European Patent Application EP 15905685.2 dated May 29, 2019.
European Office Action corresponding to European Patent Application EP 17157606.9 dated Jul. 2, 2019.
Extended European Search Report corresponding to European Patent Application EP 15908025.8 dated Jul. 2, 2019.
Extended European Search Report corresponding to European Patent Application EP 18212054.3 dated Jul. 3, 2019.
Partial Supplementary European Search Report corresponding to European Patent Application EP 16884297.9 dated Jul. 30, 2019.

* cited by examiner

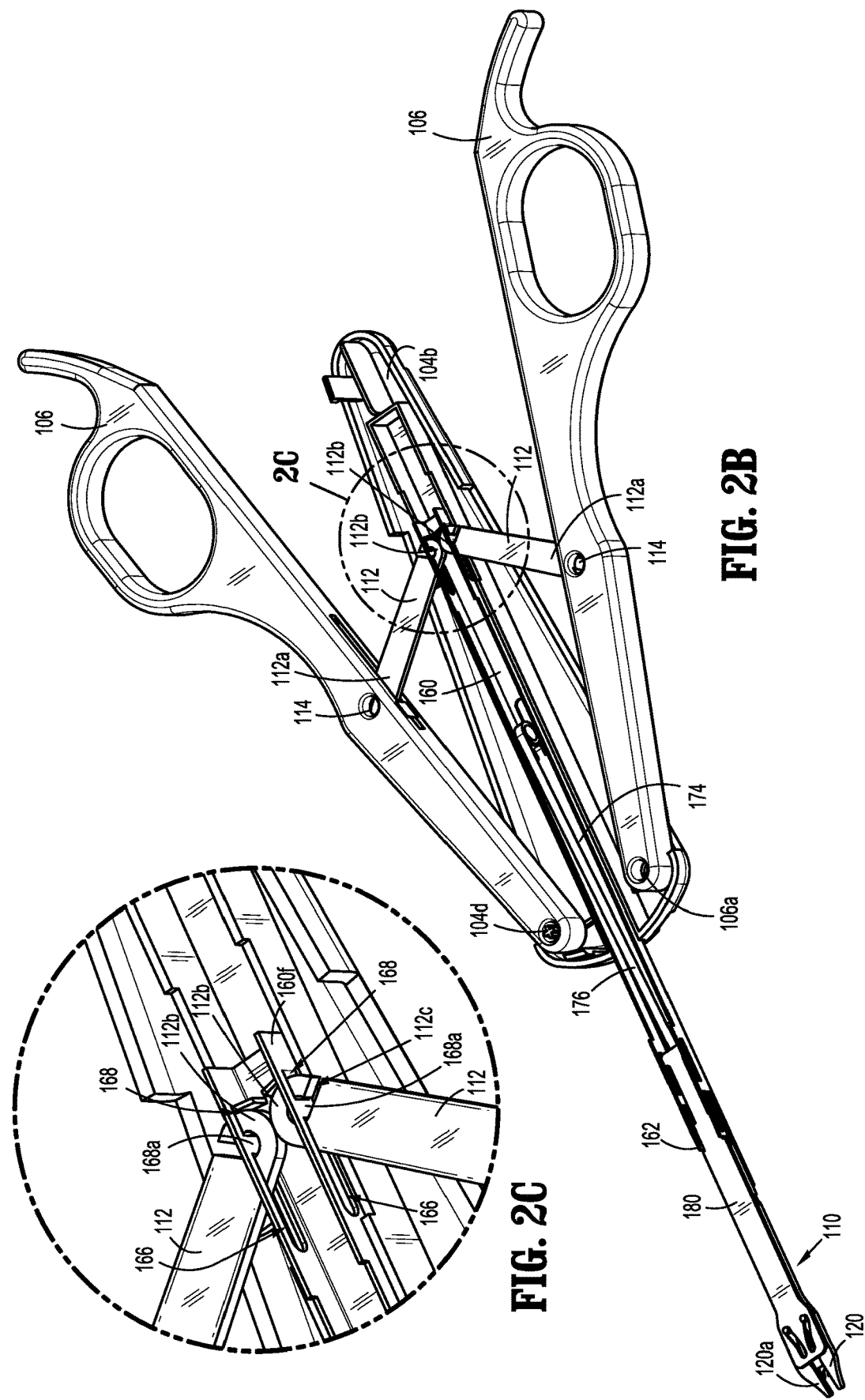

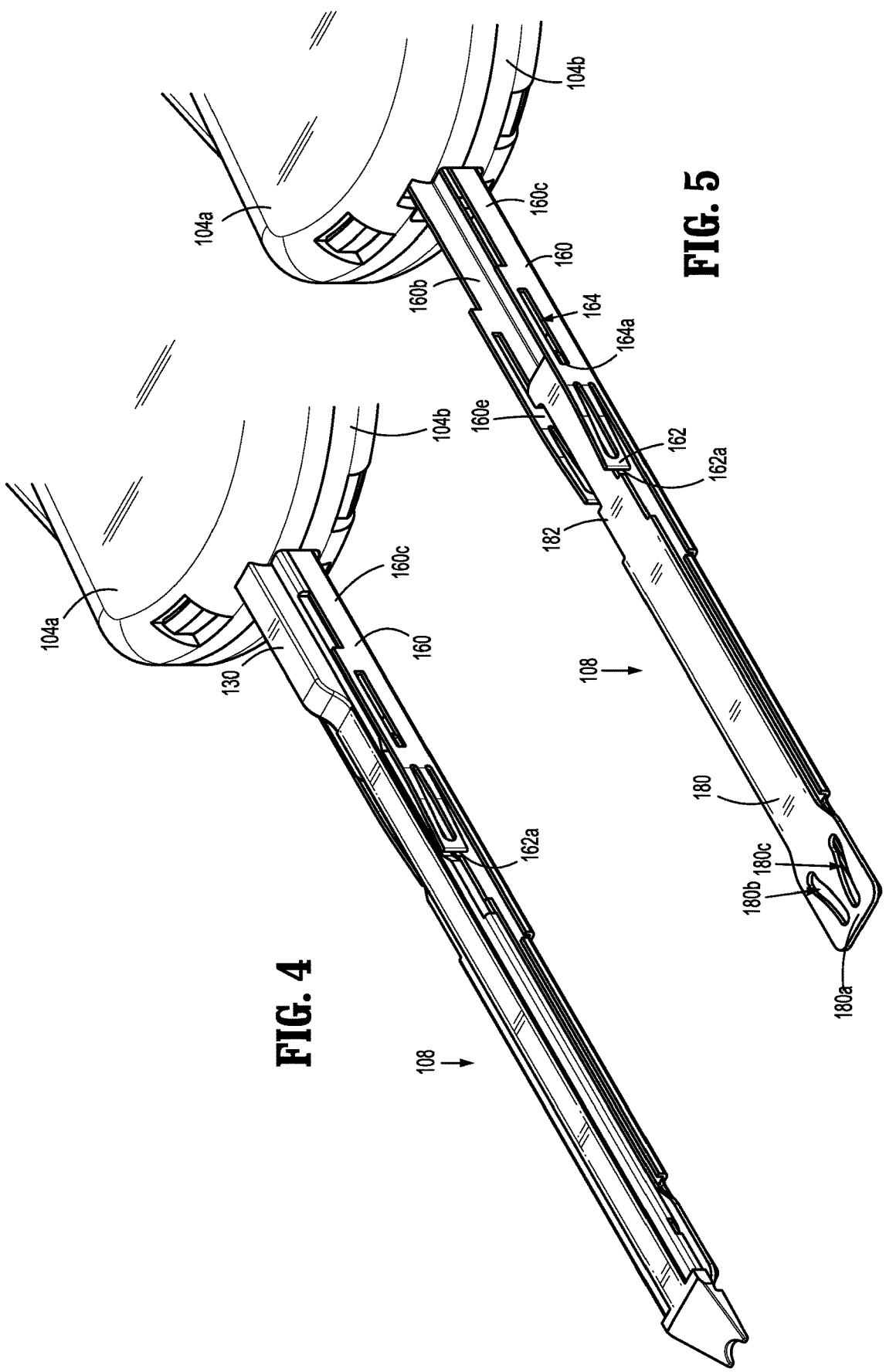

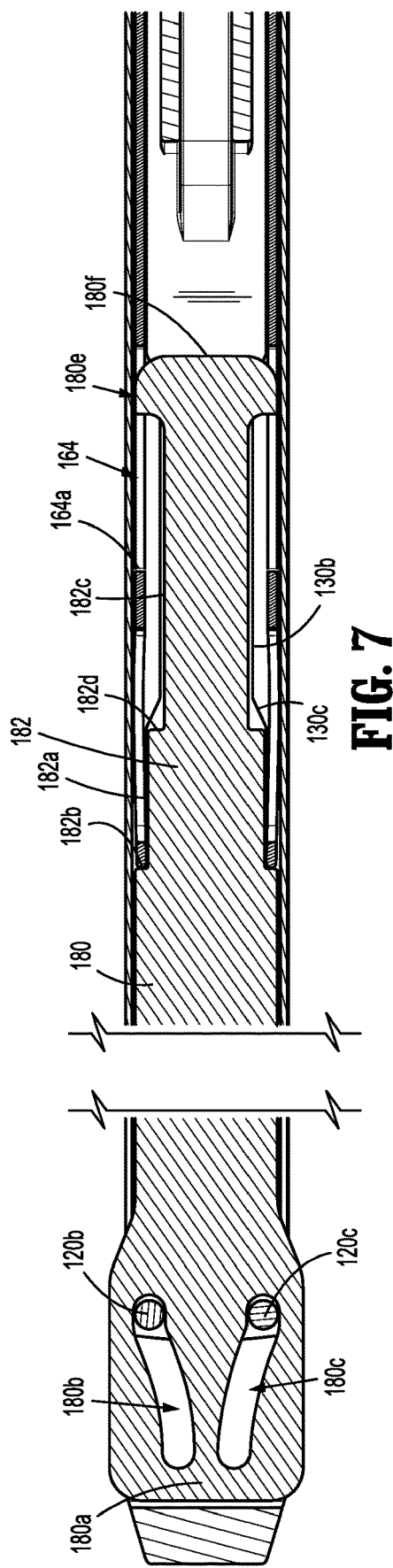
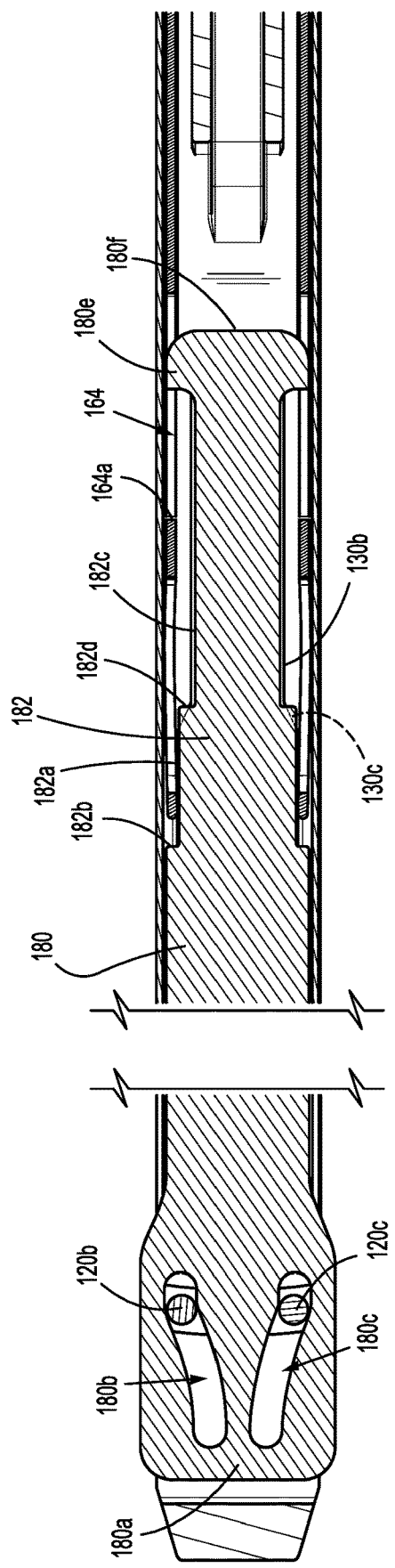

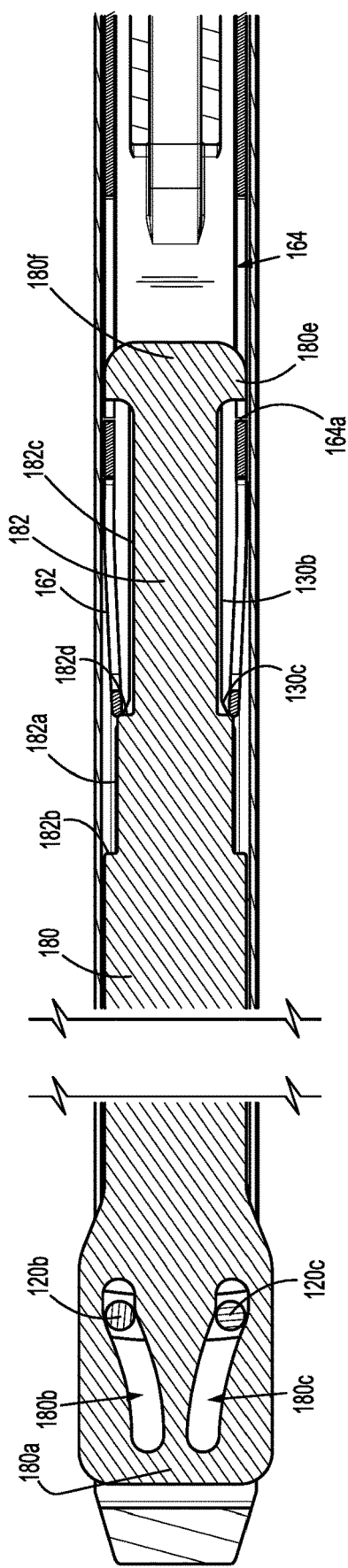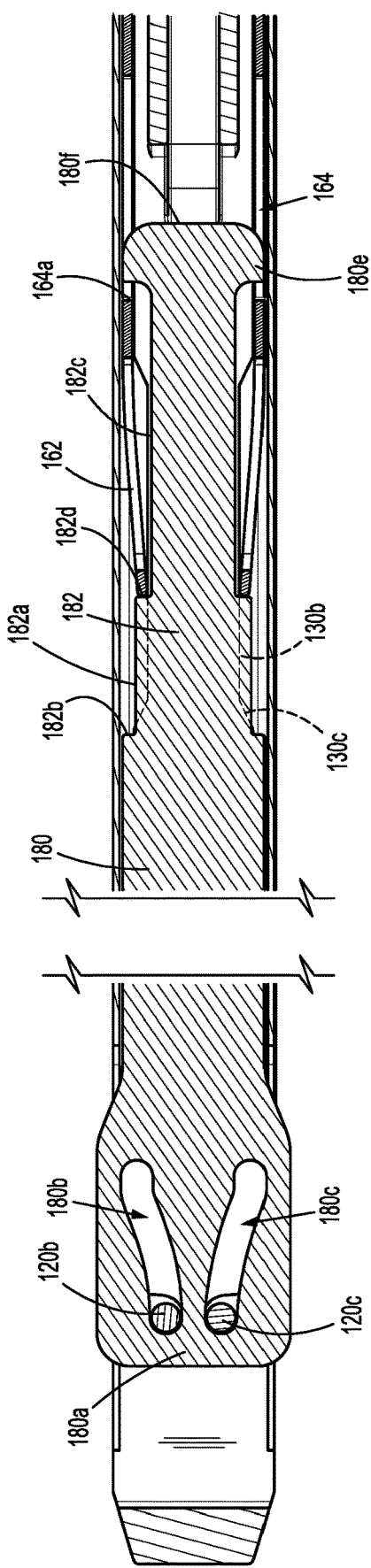

SURGICAL CLIP APPLIER

CROSS-REFERENCE TO RELATED APPLICATIONS

This application is a divisional of U.S. patent application Ser. No. 14/315,508 filed Jun. 26, 2014, now U.S. Pat. No. 9,775,624, which claims the benefit of and priority to U.S. Provisional Patent Application No. 61/870,404, filed Aug. 27, 2013, the entire disclosure of which is incorporated by reference herein.

BACKGROUND

1. Technical Field

The present application relates to surgical instruments, and more particularly, to surgical clip appliers having a plurality of clips for applying the clips to body tissues and vessels during surgical procedures.

2. Discussion of Related Art

Surgical clip appliers are known in the art and have increased in popularity among surgeons by offering an alternative to conventional suturing of body tissues and vessels. Typical instruments are disclosed in U.S. Pat. No. 5,030,226 to Green et al. and U.S. Pat. No. 5,431,668 to Burbank, III et al. the entirety of each of which is incorporated herein by reference. These instruments generally provide a plurality of clips which are stored in the instrument and which are fed sequentially to the jaw mechanism at the distal end of the instrument upon opening and closing of the handles at the proximal end of the instrument. As the handles are closed, the jaws close to form a clip positioned between the jaw members, and as the jaws are opened to release the formed clip, a new clip is fed from the series of clips to a position between the jaws. This process may be repeated up to and until all the clips in the series of clips have been used.

A need exists for clip applier having simplified operation using fewer components to provide a more efficient and cost effective clip applying device without diminishing functionality.

SUMMARY

The present application relates to surgical clip appliers having a plurality of clips for applying the clips to body tissues and vessels during surgical procedures and their methods of use.

According to an aspect of the present disclosure, a surgical clip applier is provided including a housing; at least one handle pivotably connected to the housing; a channel assembly extending distally from the housing; a clip carrier disposed within the channel assembly and defining a channel therein; a plurality of clips slidably disposed within the channel of the clip carrier; and a jaw assembly including a pair of jaws extending from an end of the channel assembly, opposite the housing. The jaw assembly is configured to accommodate a clip therein and is operable to effect formation of the clip in response to movement of the at least one handle. The surgical clip applier further includes a clip pusher bar slidably supported within at least one of the housing and the channel assembly. The clip pusher bar has a first end operatively connected to the at least one handle and at least one flexible tab. The surgical clip applier further includes a camming plate slidably supported within the channel assembly and configured to effectuate closure of the pair of jaws. The camming plate includes a lost motion portion and the flexible tab of the clip pusher bar is configured to engage the lost motion portion during an initial movement of the clip pusher bar to cause the camming plate to move with the clip pusher bar. The flexible tab of the clip pusher bar is configured to disengage from the lost motion portion during a subsequent movement of the clip pusher bar to allow the clip pusher bar to move relative to the camming plate.

In an aspect of the present disclosure, the lost motion portion of the camming plate includes a shoulder. The flexible tab is configured to engage the shoulder during the initial movement of the clip pusher bar and to disengage from the shoulder during the subsequent movement of the clip pusher bar.

In an aspect of the present disclosure, the lost motion portion includes a first recess and a second recess. The flexible tab is slidably disposed within the second recess during the initial movement of the clip pusher bar and is slidably disposed within the first recess during the subsequent movement of the clip pusher bar.

In an aspect of the present disclosure, the shoulder is located at a distal end of the second recess of the lost motion portion.

In an aspect of the present disclosure, the channel assembly includes a camming surface. The camming surface is configured to disengage the flexible tab from the lost motion portion after the initial movement of the clip pusher bar.

In an aspect of the present disclosure, the channel assembly includes a first recess and a second recess. The camming surface is disposed between the first and second recesses of the channel assembly. The flexible tab is configured to slide along the second recess during the initial movement of the clip pusher bar until the camming surface is reached. The flexible tab is configured to cam along the camming surface to disengage the flexible tab from the lost motion portion. The flexible tab is also configured to slide along the first recess during the subsequent movement of the clip pusher bar.

In an aspect of the present disclosure, the clip pusher bar further includes a second end that is configured to urge a clip from the plurality of clips to a location between the jaws.

In an aspect of the present disclosure, the clip pusher bar is moveable toward the jaw assembly to urge the clip from the plurality of clips to the location between the jaws and moveable away from the jaw assembly to effectuate closure of the pair of jaws.

In an aspect of the present disclosure, the camming plate is movable away from the jaw assembly as the handle is actuated in a first direction to effectuate closure of the jaws and is movable toward the jaw assembly as the handle is actuated in a second direction to effectuate opening of the jaws.

In an aspect of the present disclosure, the camming plate includes at least one camming slot and the jaws include at least one camming pin received within the camming slot of the camming plate.

In an aspect of the present disclosure, the camming pin cams along the camming slot to effectuate opening and closure of the jaws during movement of the camming plate.

In an aspect of the present disclosure, the flexible tab is distally oriented and inwardly biased against the lost motion portion of the camming plate.

In an aspect of the present disclosure, the camming plate includes a proximal flange and the clip pusher bar includes a distal window. The proximal flange of the camming plate is received within the distal window and engagable with a distal end of the distal window when the clip pusher bar moves proximally to move the camming plate proximally.

In an aspect of the present disclosure, the clip pusher bar includes at least one proximal window configured to receive a link member of the handle to provide the operative connection with the handle.

According to an aspect of the present disclosure, a method of operating a surgical clip applier is provided including the steps of actuating a handle of a clip applier an initial amount to cause an initial movement of a clip pusher bar of the clip applier in a first direction. A flexible tab of the clip pusher bar engages a shoulder of a camming plate of the clip applier to cause movement of the camming plate in the first direction. The camming plate effectuates an opening of a pair of jaws of the clip applier upon movement of the camming plate in the first direction. The method further includes actuating the handle of the clip applier a subsequent amount to cause a subsequent movement of the clip pusher bar of the clip applier in the first direction. The flexible tab disengages from the shoulder of the camming plate such that the clip pusher bar moves the subsequent amount in the first direction relative to the camming plate.

In an aspect of the present disclosure, the method includes the step of urging, by the clip pusher bar, a clip of a plurality of clips of the clip applier in between the jaws of the clip applier during the subsequent movement of the clip pusher bar in the first direction.

In an aspect of the present disclosure, during the subsequent movement of the clip pusher bar in the first direction, the method further includes the step of camming the flexible tab over a camming surface of a channel assembly of the clip applier to disengage the flexible tab from the shoulder of the camming plate.

In an aspect of the present disclosure, the method further includes the step of actuating the handle of a clip applier in an opposite direction to cause movement of the clip pusher bar in a second direction. The clip pusher bar engages the camming plate to move the camming plate in the section direction to effectuate a closing of the jaws.

In an aspect of the present disclosure, the method further includes the step of moving the camming plate in the second direction due to engagement of a proximal flange of the camming plate with a distal window of the clip pusher bar.

In an aspect of the present disclosure, when the clip pusher bar moves in the second direction, the flexible tab of the clip pusher bar is received within a recess of the camming plate proximate the shoulder. The flexible tab is biased against the recess of the camming plate.

Although the above aspects and embodiments are described separately for convenience and clarity, it is contemplated that the above aspects and embodiments may be combined without departing from the scope of the present disclosure.

BRIEF DESCRIPTION OF THE DRAWINGS

The present clip applier will be more fully appreciated as the same becomes better understood from the following detailed description when considered in connection with the following drawings, in which:

FIG. 2B is a perspective view of the surgical clip applier of FIG. 1 with an upper housing half of the handle assembly and a cartridge cover of a channel assembly removed;

FIG. 2C is an enlarged view of the indicated area of detail of FIG. 2B;

FIG. 4 is a top, perspective partial view which shows the channel assembly of the surgical clip applier of FIG. 1;

FIG. 5 is a top, perspective partial view which shows the channel assembly of FIG. 4, with the cartridge cover removed;

FIG. 7 is a partial cross-sectional view of the channel assembly of the surgical clip applier of FIG. 1 in an initial position prior to actuation of the handles of the handle assembly;

FIG. 8 is a partial cross-sectional view of the channel assembly of the surgical clip applier of FIG. 1 during an initial actuation of the handles;

FIG. 9 is a partial cross-sectional view of the channel assembly of the surgical clip applier of FIG. 1 during a subsequent actuation of the handles; and FIG. 10 is a partial cross-sectional view of the channel assembly of the surgical clip applier of FIG. 1 in a final position with handles fully actuated.

DETAILED DESCRIPTION OF EMBODIMENTS

Figure 1:
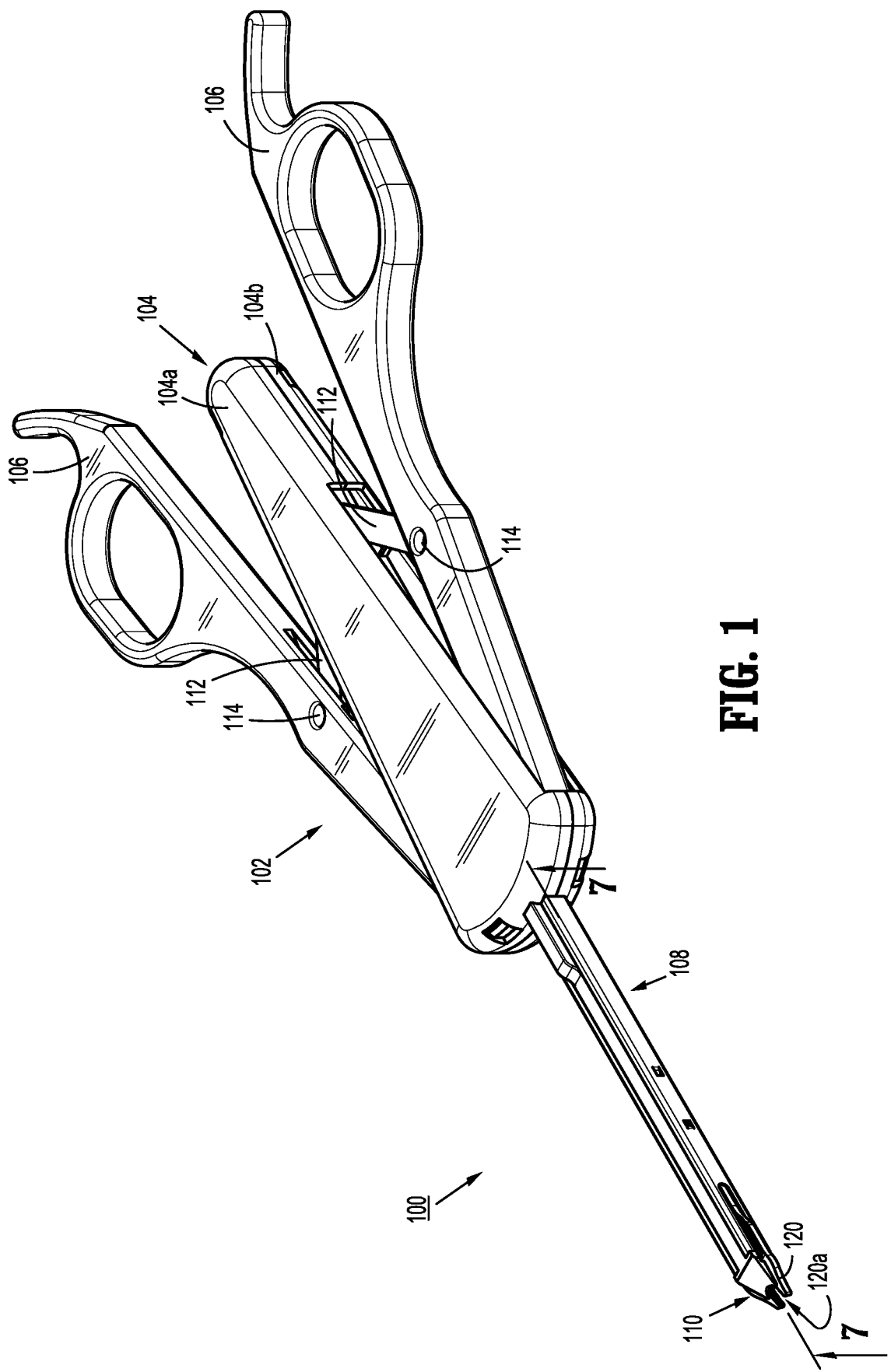
FIG. 1 is a top, perspective view of a surgical clip applier according to an embodiment of the present disclosure.

Embodiments of surgical clip appliers in accordance with the present disclosure will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Figure 2A:
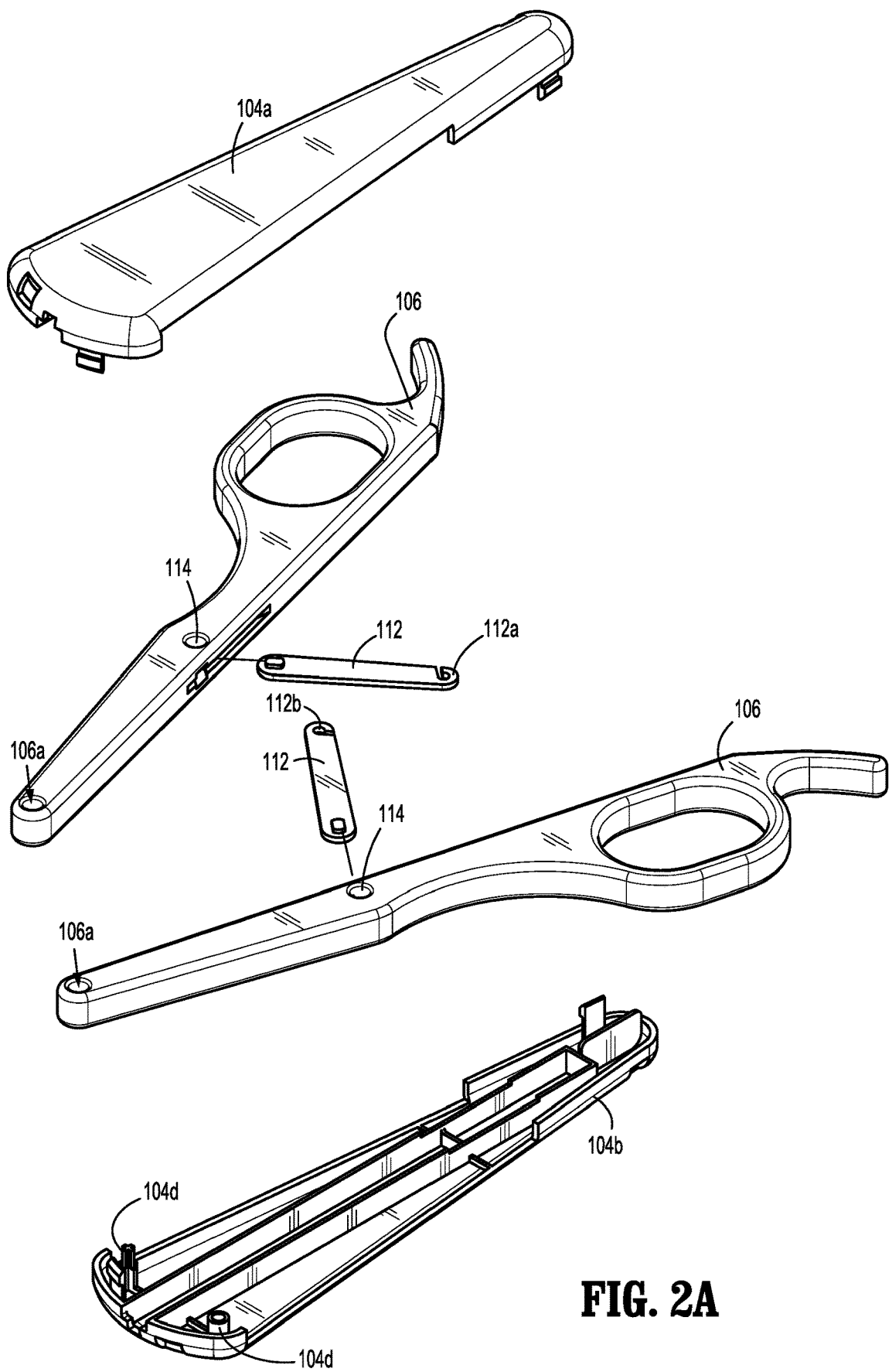
FIG. 2A is an exploded, perspective view of a handle assembly of the surgical clip applier of FIG. 1.
Figure 3:
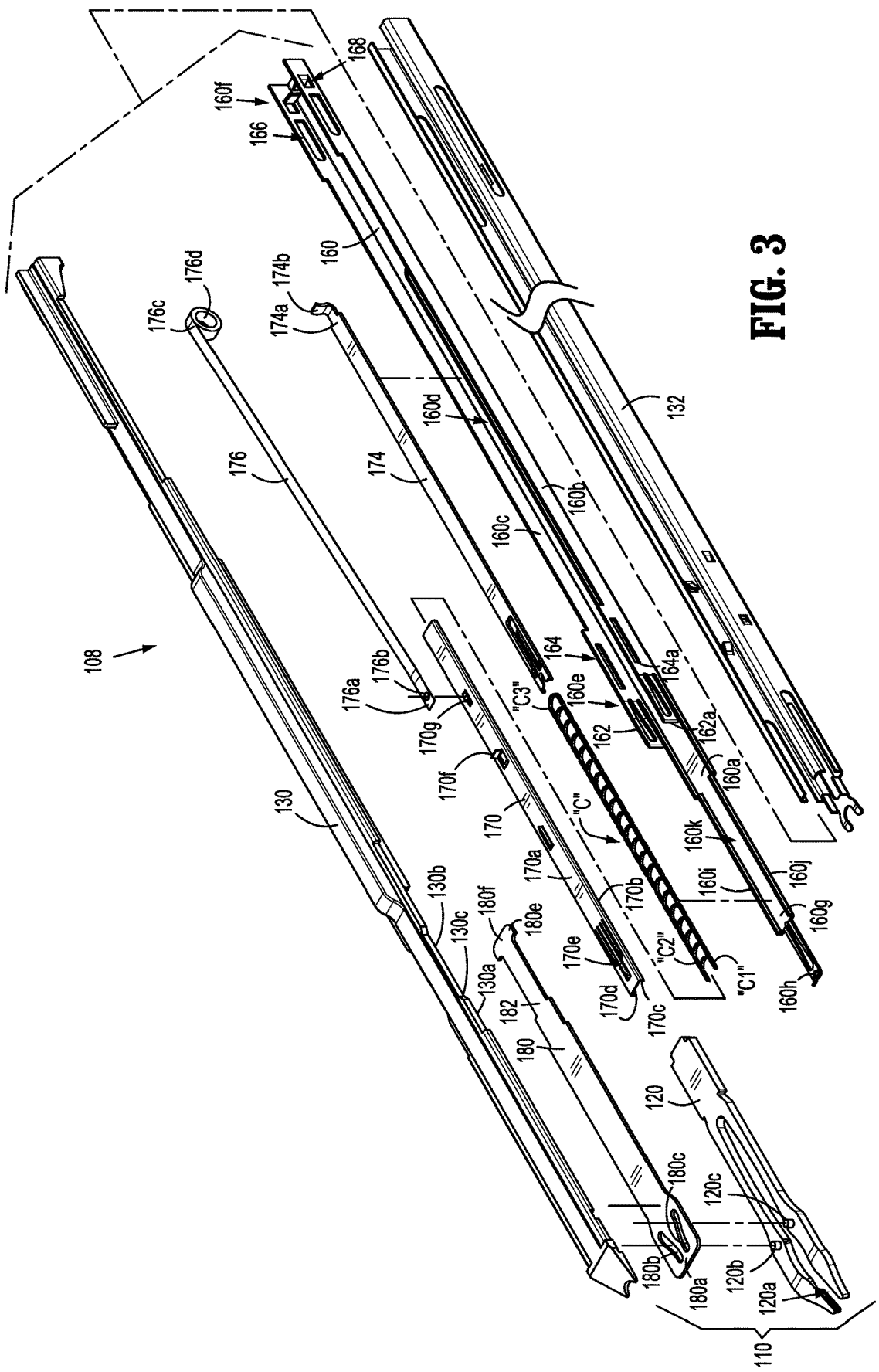
FIG. 3 is an exploded perspective view of a channel assembly of the surgical clip applier of FIG. 1.

Referring now to FIGS. 1-3, a surgical clip applier in accordance with an embodiment of the present disclosure is generally designated as 100. Surgical clip applier 100 generally includes a handle assembly 102 including a housing 104 having an upper housing half 104a and lower housing half 104b. Handle assembly 102 further includes a pair of handles 106 pivotably secured to housing 104 and extending outwardly therefrom. A channel assembly 108 is fixedly secured to housing 104 and extends distally therefrom, terminating in a jaw assembly 110 supported in a distal end of channel assembly 108. As seen in FIGS. 1 and 2A-2C, housing halves 104a and 104b of clip applier 100 fit together by, e.g., snap fit engagement with one another. Alternatively, housing halves 104a and 104b may be joined through any manner including, for example, one or more screws, fasteners and the like, through the use of glues, or other adhesives, or through the use of plastic or radiofrequency welding.

As can be seen in FIGS. 1 and 2A-2C, handles 106 are secured to housing 104 by handle pivot pins 104d extending between lower housing half 104b and upper housing half 104a through respective apertures 106a formed in handles 106. Handle assembly 102 includes a link member 112 pivotally connected to each handle 106 at a pivot point 114 formed in a respective handle 106. A proximal end 112a of each link member 112 includes a hooked or G-shaped portion 112b that is pivotally connected to clip pusher bar 160. In use, as will be described in greater detail below, as handles 106 are squeezed, link members 112 push pusher bar 160 proximally.

Referring now to FIGS. 1, 2B-2C, and 3, channel assembly 108 includes a channel or cartridge cover 130 and an outer or lower channel 132 each having a proximal end retained in housing assembly 102, between upper and lower housing halves 104a, 104b.

Clip applier 100 further includes a clip pusher bar 160 that is reciprocally supported in and extends between handle assembly 102 and channel assembly 108. A proximal portion of pusher bar 160 is supported between upper and lower housing halves 104a, 104b of housing 104 and a distal portion of pusher bar 160 is supported between cartridge cover 130 and outer channel 132 of channel assembly 108.

Referring now to FIGS. 3-6, pusher bar 160 includes a lower wall 160a and first and second side walls 160b, 160c extending from the lower wall 160a. Lower wall 160a and side walls 160b, 160c together define a channel 160d extending along at least a portion of the pusher bar 160 for at least partial reception of jaw assembly 110, a clip carrier 170, a clip follower 174, a clip spring 176 and a camming plate 180 therein.

Referring now to FIGS. 2B, 2C, and 3, first and second side walls 160b and 160c each include a pair of proximal windows 166 and 168 at a proximal end 160f for the reception of hooks 112b of linkage members 112. Proximal windows 166 and 168 include a pivot bar 168a disposed therebetween about which the linkage members 112 pivot during actuation of handles 106. Each pivot bar 168a is received within an opening 112c of the hook 112b of one of the linkage members 112 to pivotably secure the linkage member 112 to the pusher bar 160.

Referring again to FIGS. 3-6, first and second side walls 160b, 160c each include a distally oriented flexible tab 162 at a distal portion 160e and a distal window 164 which are proximal of the flexible tab 162. It is contemplated that distal windows 164 may alternatively be disposed distal of flexible tabs 162.

Pusher bar 160 further includes a distal end 160g extending distally of distal portion 160e defining a pusher 160h configured and adapted to selectively engage/move a distalmost clip "C1" of a stack of clips "C" stored in surgical clip applier 100. In an embodiment, distal end 160g of pusher bar 160 includes side walls 160i and 160j extending from lower wall 160a and defining a channel 160k for the reception of a distal portion of a clip carrier 170. In some embodiments, the side walls 160i and 160j extend a first height from lower wall 160a, and the side walls 160b and 160c extend a second height from lower wall 160a. In some embodiments, the first height of side walls 160i and 160j is less than the second height of side walls 160b and 160c.

With reference to FIG. 3, clip applier 100 further includes a clip carrier 170 disposed within channel assembly 108 and within the channel 160d of pusher bar 160. Clip carrier 170 is a generally box-like structure having an upper wall 170a, a pair of side walls 170b and a lower wall 170c defining a channel 170d therethrough.

A stack of surgical clips "C" is loaded and/or retained within channel 170d of clip carrier 170 in a manner so as to slide therewithin and/or therealong. The clips of the plurality of surgical clips "C" are arranged in tip-to-tail fashion within channel 170d. Clip carrier 170 further includes a tab 170e at a distal end of channel 170d for maintaining the distal most clip "C1" in place. Clip carrier 170 further includes a fin 170f extending from a top surface thereof for engaging cartridge cover 130 to inhibit longitudinal movement of clip carrier 170 relative to cartridge cover 130. Clip carrier 170 further includes a tab 170g for engaging an opening 176b of clip spring 176.

With further reference to FIG. 3, clip applier 100 further includes a clip follower 174 slidably disposed within channel 170d of clip carrier 170. As will be discussed in greater detail below, clip follower 174 is positioned behind the stack of surgical clips "C" and is provided to urge the stack of clips "C" forward during an actuation of clip applier 100. Clip follower 174 is biased distally against the stack of clips "C" by a clip spring 176. Spring 176 may take the form of a constant force spring or other comparable biasing element. A distal end 176a of clip spring 176 is fixedly attached or secured to clip carrier 170 by insertion of tab 170g of clip carrier 170 into opening 176b of clip spring 176. Clip spring 176 may be fixedly attached to clip carrier 170 or any other fixed surface of clip applier 100 and may be fixedly attached in any manner including, for example, one or more screws, fasteners and the like, through the use of glues, or other adhesives, or through the use of plastic or radiofrequency welding. A proximal portion 176c of clip spring 176 is wound around a spool 176d secured against a proximal end 174a of clip follower 174. In an embodiment, clip follower 174 includes a flange 174b at the proximal end 174a for engaging spool 176c. Spool 176c is biased against flange 174b by clip spring 176 to bias clip follower 174 against the stack of clips "C".

During actuation of clip applier 100, as clips "C" are used and the number of clips "C" remaining in clip carrier 170 is reduced, with distal end 176a of spring 176 fixedly secured in place, spring 176 winds-up around spool 176c to urge clip follower 174 distally against the stack of clips "C" and bias or move the stack of clips "C" within clip carrier 170.

As can be seen in FIGS. 1 and 3, jaw assembly 110 includes a pair of jaws 120 mounted on or at a distal end of channel assembly 108 and actuatable by handles 106 of handle assembly 102. Jaws 120 are formed of a suitable biocompatible material such as, for example, stainless steel or titanium.

Jaws 120 are mounted in a distal end of housing 108 such that jaws 120 are longitudinally stationary relative to outer channel 132. As seen in FIGS. 1, 2B-2C, and 3, jaws 120 define a channel 120a therebetween for receipt of a surgical clip "C" therein. Each jaw 120 further includes a respective camming pin 120b, 120c projecting therefrom.

Figure 6:
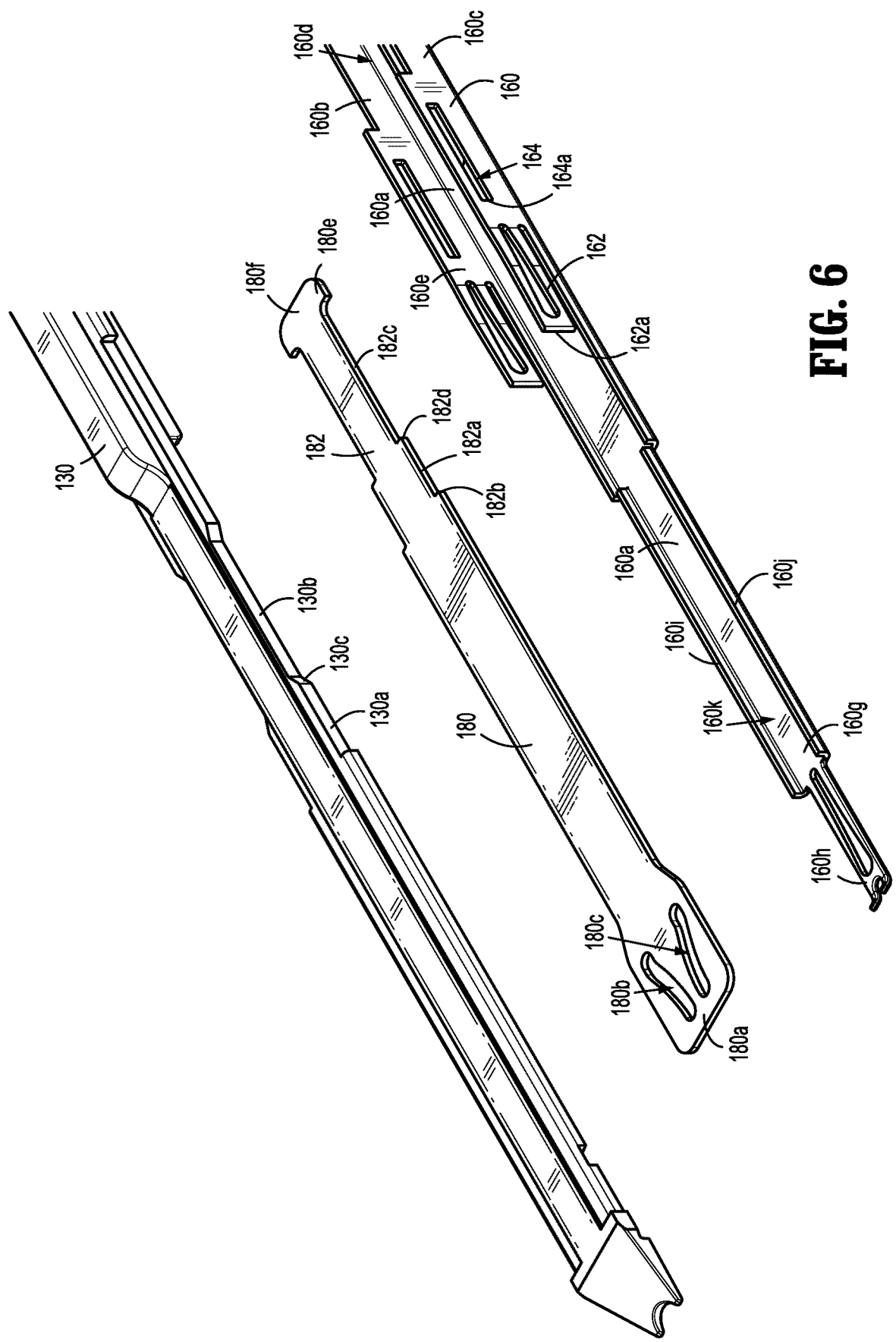
FIG. 6 is an exploded partial view illustrating the cartridge cover, camming plate, and clip pusher bar of the channel assembly of FIG. 4.

As can be seen in FIGS. 3, 5 and 6, jaw assembly 110 further includes a camming plate 180 disposed within housing 108. Camming plate 180 is slidably received within channel 160a of pusher bar 160 and includes a distal end 180a having first and second camming slots 180b, 180c that slidably receive camming pins 120b, 120c of jaws 120, respectively. Camming plate 180 is configured to actuate the jaws 120 upon actuation of handles 106.

During actuation of clip applier 100, as camming plate 180 moves proximally, camming pins 120b, 120c of jaws 120 travel along camming slots 180b, 180c of camming plate 180 to effectuate closure of the jaws 120 and to form the distal most clip "C1" located or loaded between the jaws 120.

Camming plate 180 further includes a lost motion section 182 having a first recessed portion 182a defining a first shoulder 182b at a distal end thereof, and a second recessed portion 182c recessed relative to the first recess portion 182a and defining a second shoulder 182d at a distal end thereof. First and second recessed portions 182a and 182c are configured and dimensioned to slidably receive flexible tabs 162 of pusher bar 160 therein during actuation of clip applier 100. Flexible tabs 162 of pusher 160 are distally oriented and inwardly biased such that when pusher bar 160 and camming plate 180 are in a proximal most position (FIG. 9), flexible tabs 162 are biased against second recessed portion 182c, proximal of or abutting second shoulder 182d thereof. In this manner, as pusher bar 160 moves distally, flexible tabs 162 engage against second shoulder 182d and drive camming plate 180 distally.

Camming plate 180 further includes a proximal flange 180e at a proximal end 180f thereof. Proximal flange 180e is slidably received within windows 164 of pusher bar 160. During actuation of clip applier 100, as pusher bar 160 is moved proximally, proximal flange 180e of camming plate 180 engages a distal end 164a of each window 164 to also move camming plate 180 proximally.

Referring now to FIGS. 3-6, cartridge cover 130 further includes first recessed portions 130a, and second recessed portions 130b recessed relative to the first recessed portions 130a. Between the first and second recessed portions 130a, 130b are camming surfaces 130c which are configured to engage against the flexible tabs 162 of pusher bar 160 during distal movement of pusher bar 160 to urge flexible tabs 162 out of second recessed portion 182c of camming plate 180 and into first recessed portion 182a of camming plate 180 to allow the pusher bar 160 to advance distally relative to camming plate 180 to thereby position the distal most clip "C1" between the jaws 120. Thus, when distal ends 162a of flexible tabs 162 are engaged against camming surfaces 130c and slide along camming surfaces 130c, flexible tabs 162 are disengaged from second shoulders 182d of camming plate 180.

Surgical clip applier 100 may include a lockout mechanism (not shown) disposed in channel assembly 108. The lockout mechanism may be actuated by clip follower 174 when a proximal most or final clip "C3" (FIG. 3) is expelled from clip applier 100. The lockout mechanism may be urged by clip follower 174 to extend across a path of pusher bar 160, thereby preventing pusher bar 160 from moving proximally and/or distally. Examples of a variety of suitable lockout mechanisms, for use in clip applier 100, can be found in U.S. Patent Publication No. 2010/0049216, filed on Aug. 13, 2009, entitled "Surgical Clip Applier and Method of Assembly," the entirety of which is incorporated herein by reference.

Surgical clip applier 100 may further include a counter mechanism (not shown) supported in at least one of the housing 104 and the channel assembly 108. The counter mechanism may be configured and adapted to display a change in the clip applier, e.g., increment or decrement, upon each actuation of handles 106. An example of a suitable counter mechanism, for use in clip applier 100, can be found in U.S. Patent Publication No. 2010/0049216, filed on Aug. 13, 2009, entitled "Surgical Clip Applier and Method of Assembly," the entirety of which is incorporated herein by reference.

Surgical clip applier 100 may further include a ratchet mechanism (not shown) including a rack having a plurality of teeth and a pawl having at least one tooth and configured to selectively engage the rack. The ratchet mechanism may be configured to inhibit inadvertent return of the pusher bar 160 before full actuation of the handles 106. An example of a suitable ratchet mechanism, for use in clip applier 100, can be found in U.S. Patent Publication No. 2010/0049216, filed on Aug. 13, 2009, entitled "Surgical Clip Applier and Method of Assembly," the entirety of which is incorporated herein by reference.

Surgical clip applier 100 may further include a pusher bar biasing member (not shown) configured to bias pusher bar 160 distally and maintain the handles 106 in an un-squeezed condition absent an applied closing force. An example of a similar biasing member, for use in clip applier 100, which can provide a compression or tension force against clip pusher bar to bias clip pusher bar distally can be found in U.S. Patent Publication No. 2010/0049216, filed on Aug. 13, 2009, entitled "Surgical Clip Applier and Method of Assembly," the entirety of which is incorporated herein by reference.

With reference to FIGS. 2B-2C and 7-10, the operation of the clip applier 100 is provided. Referring now to FIGS. 2B and 7, prior to any initial squeezing of handles 106 of clip applier 100, in an initial or original position, with a first of clips "C" loaded into the jaws 120, the pusher bar 160 and camming plate 180 are each located in a distal-most position with flexible tabs 162 of pusher bar 160 disposed in first recessed portion 182a of camming plate 180 and abutting or proximate to first shoulder 182b thereof. With reference to FIG. 6, in the initial or original position, proximal flange 180e of camming plate 180 is located at the proximal end of window 164 of pusher bar 160.

Referring now to FIGS. 2B, 8 and 9, the operation associated with an initial squeezing of handles 106 of clip applier 100 will be described. As illustrated in FIG. 2C, as handles 106 are squeezed an initial amount, link members 112 push pusher bar 160 proximally.

As illustrated in FIGS. 8 and 9, during the initial squeezing of handles 106, as pusher bar 160 translates proximally, flexible tabs 162 slide proximally along first recessed portion 182a of camming member 180 and first recessed portion 130a of cartridge cover 130 until flexible tabs 162 reach camming surfaces 130c of cartridge cover 130. As flexible tabs 162 slide over camming surfaces 130c, flexible tabs 162 engage against second recessed portion 182c of camming member 180 proximal of second shoulder 182d and second recessed portion 130b of cartridge cover 130 due to the inward biasing of flexible tabs 162.

As pusher bar 160 continues to translate proximally, proximal flange 180e of camming plate 180 engages distal end 164a of window 164 of pusher bar 160 thereby causing camming plate 180 to also translate proximally.

Referring now to FIGS. 9 and 10, the operation associated with a further continued squeezing of handles 106 of clip applier 100 will be described. As handles 106 are squeezed a subsequent amount, pusher bar 160 continues to translate proximally. As pusher bar 160 translates proximally, camming plate 180 translates proximally due to the engagement of flange 180e thereof with the distal end 164a of each window 164, and camming pins 120b and 120c of jaw assembly 110 travel along camming slots 180b and 180c of camming plate 180 to actuate the jaws 120 from an open configuration with camming pins 120b and 120c space apart (FIG. 7) to a closed configuration with camming pins 120b and 120c approximated toward one another (FIG. 10) to form a surgical clip "C" positioned within the jaws 120.

Referring now to FIG. 10, the state of clip applier 100 with handles 106 in the fully squeezed position will now be described. As illustrated in FIG. 10, with handles 106 in the fully squeezed position, pusher bar 160 and camming plate 180 are at proximal most positions with camming pins 120b and 120c at the distal end of camming slots 180b and 180c, respectively, with jaws 120 approximated together in the closed configuration to form a clip "C" disposed between jaws 120 about tissue or a vessel. Flexible tabs 162 of pusher bar 160 are biased against second recessed portion 180c of camming plate 180 and second recessed portion 130b of cartridge cover 130 with the distal end 162a of flexible tabs 162 located proximal of second shoulder 182d and camming surfaces 130c. In the fully squeezed position, proximal flange 180e of camming plate 180 is located at a distal end 164a of distal window 164a.

Once the distal most clip "C1" has been formed about the tissue or vessel, handles 106 are released or un-squeezed. With reference to FIGS. 6-10 in reverse order, the operation associated with the releasing of handles 106 will now be described.

As illustrated in FIG. 2C, as handles 106 are released an initial amount, link members 112 pull pusher bar 160 distally.

As illustrated in FIGS. 9 and 10, during the initial release of handles 106, as pusher bar 160 translates distally, distal ends 162a of flexible tabs 162 engage against second shoulders 182d of camming plate 180 to also move camming plate 180 distally. As camming plate 180 moves distally, pins 120b and 120c of jaws 120 travel proximally along to camming slots 180b and 180c to begin opening or un-approximating jaws 120.

As illustrated in FIGS. 8 and 9, during continued releasing of handles 106, as pusher bar 160 and camming plate 180 continue to move distally, camming pins 120b and 120c of jaws 120 reach the proximal ends of camming slots 180b and 180c and the jaws 120 are in an un-approximated or open configuration and ready to receive the next clip "C".

During the further releasing of handles 106, as pusher bar 160 moves distally relative to cartridge cover 130, distal ends 162a of flexible tabs 162 slide along camming surfaces 130c of cartridge cover 130 and are flexed outward relative to second recess 182c of camming plate 180 and second recess 130b of cartridge cover 130 and into first recess 182a of camming plate 180 and first recess 130a of cartridge cover 130. In this manner distal ends 162a of flexible tabs 162 are disengaged from second shoulder 182d of camming plate 180.

As illustrated in FIGS. 7 and 8, during a further continued releasing of handles 106 pusher bar 160 continues to translate distally with distal ends 162a of flexible tabs 162 sliding along first recess 182a of camming plate 180 and first recess 130a of cartridge cover 130. Because distal ends 162a of flexible tabs 162 are no longer engaged against second shoulder 182d of camming plate 180, camming plate 180 is no longer translated distally by pusher bar 160 and pusher bar 160 is allowed to further translate distally relative to camming plate 180.

During the continued distal translation of pusher bar 160, pusher 160h engages a new distal most clip "C2" and urges the new distal most clip "C2" between jaws 120. Once the new distal most clip "C2" has been urged between jaws 120, clip follower 174 advances the stack of clips "C" due to the biasing of clip biasing member 176.

Once handles 106 have been fully released, clip applier 100 has been returned to the initial or original position with clip "C2" loaded between jaws 120 and pusher bar 160 and camming plate 180 in the distal most positions. The clip applier 100 is now ready to apply and form clip "C2" to tissue or another vessel in the manner described above for clip "C1".

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A method of operating a surgical clip applier comprising:
   actuating a handle of the clip applier in a first handle direction by an initial amount to cause an initial movement of a clip pusher bar of the clip applier in a first clip-pusher-bar direction, such that a flexible tab of the clip pusher bar engages a shoulder of a camming plate of the clip applier to cause movement of the camming plate in the first clip-pusher-bar direction, the camming plate effectuating an opening of a pair of jaws of the clip applier upon movement of the camming plate in the first clip-pusher-bar direction;
   actuating the handle of the clip applier in the first handle direction by a subsequent amount to cause a subsequent movement of the clip pusher bar of the clip applier in the first clip-pusher-bar direction, such that the flexible tab disengages from the shoulder of the camming plate such that the clip pusher bar moves the subsequent amount in the first clip-pusher-bar direction relative to the camming plate;
   actuating the handle of the clip applier in a second handle direction, opposite to the first handle direction, to cause movement of the clip pusher bar in a second clip-pusher-bar direction and engaging the camming plate with the clip pusher bar to move the camming plate in the second clip-pusher-bar direction to effectuate closing of the pair of jaws; and
   moving the camming plate in the second clip-pusher-bar direction due to engagement of a proximal flange of the camming plate with a distal window of the clip pusher bar.

2. The method of claim 1, further comprising:
   urging, by the clip pusher bar, a clip of a plurality of clips of the clip applier in between the pair of jaws of the clip applier during the subsequent movement of the clip pusher bar in the first clip-pusher-bar direction.

3. The method of claim 1, wherein during the subsequent movement of the clip pusher bar in the first clip-pusher-bar direction, the method further comprising:
   camming the flexible tab over a camming surface of a channel assembly of the clip applier and disengaging the flexible tab from the shoulder of the camming plate.

4. The method of claim 1, wherein when the clip pusher bar moves in the second clip-pusher-bar direction, the method further comprising:
   receiving the flexible tab of the clip pusher bar within a recess of the camming plate proximate the shoulder and biasing the flexible tab against the recess of the camming plate.

5. The method of claim 1, further comprising:
   locating a distal end portion of the distal window of the clip pusher bar adjacent the proximal flange of the camming plate to move the camming plate in the second clip-pusher-bar direction.

6. A method of operating a surgical clip applier, comprising:
   moving a clip pusher bar of the clip applier a first initial amount in a first direction and engaging a lost motion portion of a camming plate of the clip applier with a flexible tab of the clip pusher bar to cause movement of the camming plate in the first direction and effectuating an opening of a pair of jaws of a jaw assembly of the clip applier upon movement of the camming plate in the first direction;

moving the clip pusher bar of the clip applier a first subsequent amount in the first direction and engaging a camming surface of the clip applier with the flexible tab of the clip pusher bar such that the flexible tab disengages from the lost motion portion of the camming plate to allow the clip pusher bar to move the first subsequent amount in the first direction relative to the camming plate;

engaging a first shoulder of the lost motion portion between a first recess and a second recess of the lost motion portion of the camming plate while the flexible tab of the clip pusher bar is positioned within the first recess to cause movement of the camming plate in the first direction; and sliding the flexible tab of the clip pusher bar along the camming surface of the clip applier and flexing the flexible tab outward relative to the first recess of the lost motion portion of the camming plate to disengage the flexible tab from the first shoulder of the lost motion portion.

7. The method of claim 6, further comprising:

sliding the flexible tab of the clip pusher bar along the second recess of the lost motion portion of the camming plate towards a second shoulder at a distal end portion of the second recess and moving the clip pusher bar the first subsequent amount in the first direction relative to the camming plate.

8. The method of claim 7, further comprising:

moving the clip pusher bar relative to the camming plate a second initial amount in a second direction, opposite from the first direction, while the flexible tab of the clip pusher bar is positioned within the second recess of the lost motion portion of the camming plate, and sliding the flexible tab along the camming surface of the clip applier to position the flexible tab within the first recess of the lost motion portion of the camming plate.

9. The method of claim 8, further comprising:

moving the clip pusher bar a second subsequent amount in the second direction; and engaging a proximal flange of the camming plate with a distal end portion of a window of the clip pusher bar to move the camming plate in the second direction with the clip pusher bar.

10. The method of claim 9, further comprising:

sliding a pair of camming pins of the jaw assembly along a corresponding pair of camming slots of the camming plate in the first direction as the camming plate moves in the second direction; and moving the pair of camming pins of the jaw assembly from a spaced-apart position towards an approximated position to effectuate closing of the pair of jaws of the jaw assembly.

\* \* \* \* \*